(12) United States Patent
Van Dun

(10) Patent No.: US 8,119,342 B2
(45) Date of Patent: Feb. 21, 2012

(54) NON-DESTRUCTIVE PROCEDURE FOR THE ISOLATION OF DNA FROM PLANTS

(75) Inventor: Cornelis Maria Petrus Van Dun, Roosendaal (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 728 days.

(21) Appl. No.: 12/191,626

(22) Filed: Aug. 14, 2008

(65) Prior Publication Data

US 2009/0111978 A1  Apr. 30, 2009

Related U.S. Application Data

(63) Continuation-in-part of application No. PCT/EP2007/001435, filed on Feb. 14, 2007.

(30) Foreign Application Priority Data

Feb. 14, 2006 (EP) .................................... 06075306
Dec. 7, 2006 (EP) .................................... 06025322

(51) Int. Cl.
  *C12Q 1/68* (2006.01)
(52) U.S. Cl. ...................................... 435/6.1
(58) Field of Classification Search ................ 435/91.1, 435/6, 200, 270, 254.3, 6.1; 536/25.41
See application file for complete search history.

(56) References Cited

U.S. PATENT DOCUMENTS

2006/0134617 A1 *  6/2006  Manen et al. ..................... 435/6

OTHER PUBLICATIONS

Lindy A. Brigham, et al., Root Border Cells as Tools in Plant Cells Studies, Methods in Cell Biology (1995) vol. 49, p. 377-387.
Lindy A. Brigham, et al., Differential Expression of Proteins and mRNAs From Border Cells and Root Tips of Pea, Plant Physiol. (1995) vol. 109, p. 457-463.
Lindy A. Brigham, et al., Isolation of Cell-Specific CDNAS From a Pea Root Border Cell Library, Plant Physiol. (1993) vol. 102, No. 1 Suppl., p. 151.
N.P. Goldberg, et al., Specific Attraction to and Infection of Cotton Root Cap Cells by Zoospores of *Pythium dissotocum*, Can. J. Bot. (1989) vol. 67, p. 1760-1767.
Martha C. Hawes, et al., The Role of Root Border Cells in Plant Defense, Trends in Plant Science (2000) vol. 5, No. 3, p. 128-133.
Martha C. Hawes, et al., Root Organogenesis From Single Cells Released From the Root Cap of *Medicago* sp., Plant Cell, Tissue and Organ Culture (1991) vol. 27, p. 303-308.
Long-Fang Oliver Chen, et al., Reproducibility of the Differential Amplification Between Leaf and Root DNAs in Soybean Revealed by RAPD Markers, Tehor. Appl. Genet (1997) vol. 95, p. 1033-1043.

* cited by examiner

*Primary Examiner* — Kent L Bell
(74) *Attorney, Agent, or Firm* — Vedder Price P.C.; Thomas J. Kowalski; Deborah L. Lu

(57) ABSTRACT

Provided is a method for obtaining DNA from a plant by collecting the root border cells from a growing root and extracting DNA from the root border cells. Preferably, the root border cells are contained in the root exudate of the growing root, which is growing in a medium, for example, water, tissue culture medium, or soil. Suitably, the root is part of a germinating seed, or the root of a seedling, or the adventitious root of a tissue culture plant or plant part.

12 Claims, 26 Drawing Sheets

NON-DESTRUCTIVE PROCEDURE FOR THE ISOLATION OF DNA FROM PLANTS

CROSS-REFERENCE TO RELATED APPLICATIONS

This application is a continuation-in-part of International application no. PCT/EP2007/001435, filed on Feb. 14, 2007, published as WO 2007/093448 on Aug. 23, 2007, and claiming priority to EP 06075306.8, filed on Feb. 14, 2006, and to EP 06025322.6, filed on Dec. 7, 2006.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a non-destructive procedure for the isolation of DNA from plants and the application of the procedure in the genetic analysis of plants or plant populations.

BACKGROUND OF THE INVENTION

Plant breeding depends on efficient exploitation of genetic variation, residing in the germplasm of a particular crop species, which determines the phenotype of a plant within a specific environment. Whereas this is traditionally done by selection of a combination of desirable traits observed at the phenotypic level, this can increasingly be performed by selection on the basis of molecular markers which are genetically closely linked to the allelic form of a gene which contributes to the expression of a specific trait.

Selection of traits on the basis of molecular markers is independent of the developmental stage of a plant and independent of the environment, which significantly enhances the selection process. The number of traits including complex traits controlled by multiple genes which can be selected upon using molecular markers has strongly increased and it can be envisaged that this development will continue at increasing pace.

Another tendency in the field of plant breeding arises form reverse genetics. Reverse genetics relates to an approach in which genes are isolated and their function is determined by modifying their primary structure or expression. With the current increase in knowledge on gene function, especially in model systems like *Arabidopsis thaliana*, reverse genetics approaches in crop systems currently gain in efficacy.

In order to determine allelic variability of candidate genes a plethora of DNA diagnostic tools are available and known to the person skilled in the art. Large populations of plants containing natural or induced allelic variation need to be screened for DNA polymorphisms at the locus of interest to acquire a saturated collection of allelic variants. Allelic forms of genes thus found can be assessed for their contribution to a plant phenotype by association studies.

The cost of screening breeding or mutant populations is largely determined by labour required to grow and sample individual plants of the population under investigation and to prepare DNA from these samples. In case a population is made available as seed samples representing the genetic variation residing within individual plants of the population under investigation, significant labour has been invested in harvesting seeds plant by plant as related individuals in families. Moreover, this exercise requires reiteration for each additional population being produced and assessed for allelic variants at specific genetic loci.

SUMMARY OF THE INVENTION

It is the object of the present invention to provide an efficient procedure for the isolation of DNA from plants. It is a further object of the invention to provide an efficient DNA isolation procedure which allows the screening of plant populations for the presence of allelic variants at specific genetic loci which makes the requirement for manual dissection of tissue samples or the requirement to harvest seeds from each individual plant of the population which is being investigated superfluous.

According to the invention it was found that such method can be based on the use of exudate released from roots, preferably from the roots of very young plants like seedlings or the roots emerging from germinating seeds or the adventitious roots of plants growing in tissue culture, to isolate DNA therefrom. More in particular, the method utilises the so-called root border cells, which detach from the root tip, as the primary source of DNA. Root border cells are living cells that surround root apices of most plant species. A plant naturally detaches the root border cells from roots, both when growing in soil as well as when growing in liquid or solid medium. Thus, the method of the present invention is considered to be non-destructive. The cells are already detached from the plant in a natural manner and can be harvested by gentle agitation and removing the medium, usually fluid, that surrounds the roots and comprises the root border cells. The growing roots keep producing root border cells that can then again be harvested at a later stage.

The invention thus relates to a method for isolating DNA from a plant comprising:
  a) collecting the root border cells from a growing root; and
  b) extracting DNA from the root border cells.

In principle, the DNA can be obtained from all root border cells. It is however very practical to collect the root border cells from a root which is part of a germinating seed. The seeds can be imbibed in a liquid medium such as water after which they germinate. Plants can thus be analysed in a very early stage of plant development, i.e. during seed germination. There is no need to wait until leaves have grown on the plant. However, the method can also be performed with root border cells from the root of a seedling.

It was furthermore found that adventitious roots grown on plant material in tissue culture produce root border cells. According to the invention these root border cells can also be used to isolate DNA therefrom.

Various methods for extracting DNA are available and known to the person skilled in the art, such as CTAB (Doyle JJ and Doyle JL (1990) Focus 12, 13-15), KingFisher96™ (Thermo Labsystems), etc.

The DNA thus obtained can be of nuclear and cytoplasmic origin and can be analysed using different nucleic acid analysis technologies. Such analysis technologies are well known to the person skilled in the art and include but are not limited to Polymerase Chain Reaction (PCR), Sanger sequencing, minisequencing, pyrosequencing, GS20 sequencing, Amplified Fragment Length Polymorphism (AFLP), Restriction Fragment Length Polymorphism (RFLP), Random Amplification of Polymorphic DNA (RAPD), Invader, Oligonucleotide Ligation Assay (OLA), Single Feature Polymorphism (SFP).

The invention further relates to the use of the novel non-destructive DNA isolation procedure for screening large populations of plants with a very high efficiency for genetic variation at particular loci. This genetic variation can either be natural or artificially induced.

The DNA isolation procedure from plants thus provided is an efficient tool to obtain DNA that can be used to detect genetic variants of specific genes in populations of plants generated through chemical or physical mutagenesis. Alternatively, the genetic variants can reside in natural populations.

The use of the method of the invention eliminates the need to set up M2 families derived from mutagenised M1 plants. Bulked M2 populations can be used instead which allows to analyse M2 populations in a more efficient and flexible manner for the presence of different allelic forms of specific genes.

The procedure for DNA isolation from plants of the invention is also suitable for use in the genetic typing of populations of plants which is useful for quality control purposes of commercial seed lots in order to assess the genetic purity and identity.

The DNA isolation procedure can furthermore be used for the identification of plants which reside in a population of genetically distinct plants on the basis of the detection of an allelic form of a polymorphic molecular marker which is linked to an allelic form of a gene which determines the expression of a certain phenotypic trait.

BRIEF DESCRIPTION OF THE DRAWINGS

The Examples refer to the following figures.

Lane 1: cucumber root border cell preparations derived from adventitious roots (BC)

Lane 2: DNA from a cucumber leaf disc, Lane 3: negative control, water.

Figure 21:
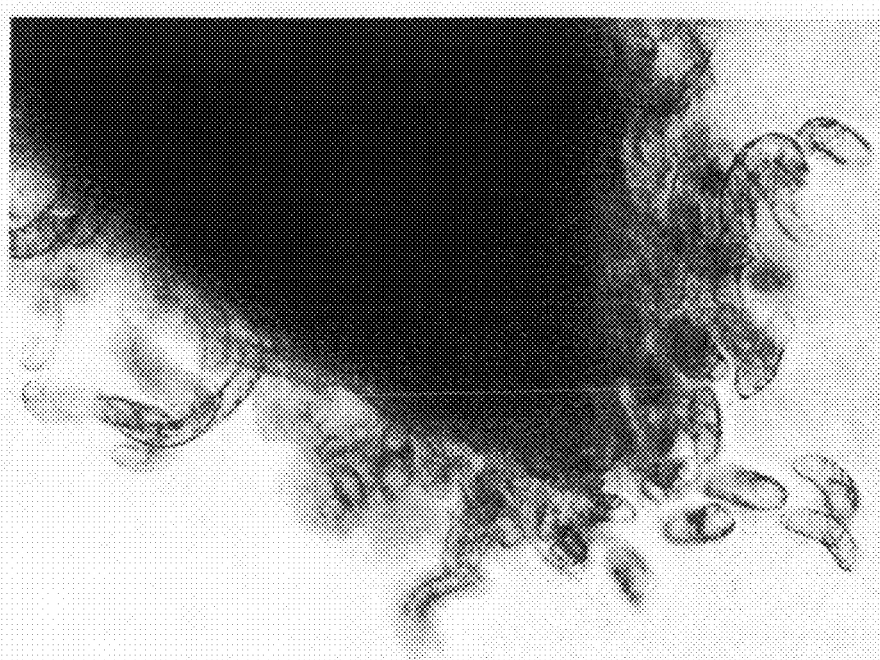
Figure 21:
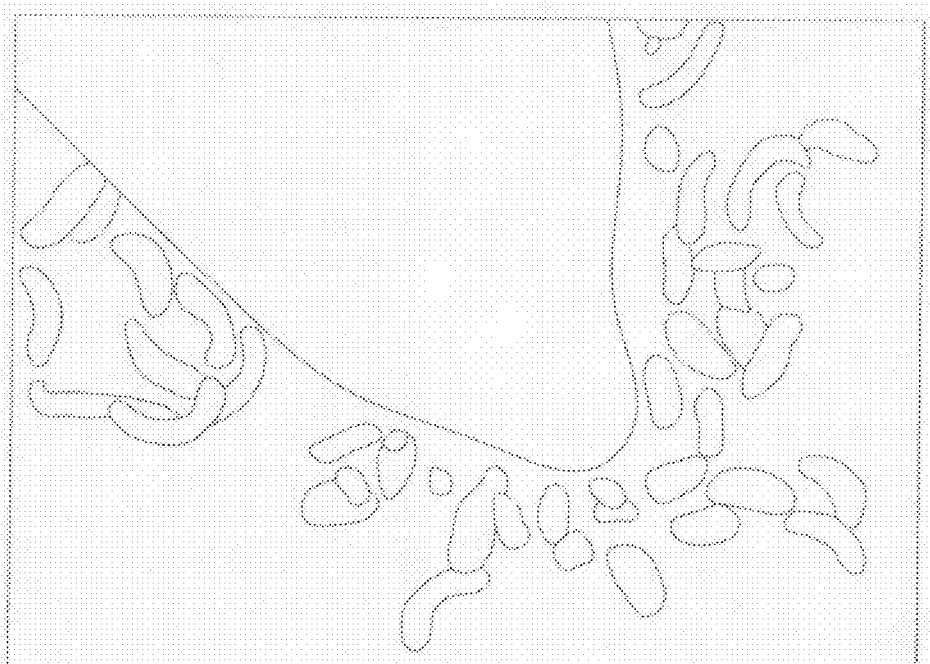

FIG. 21(a) shows a root tip of pepper shedding root border cells into the liquid medium; FIG. 21(b) shows a schematic depicting the image of FIG. 21(a).

Figure 22:
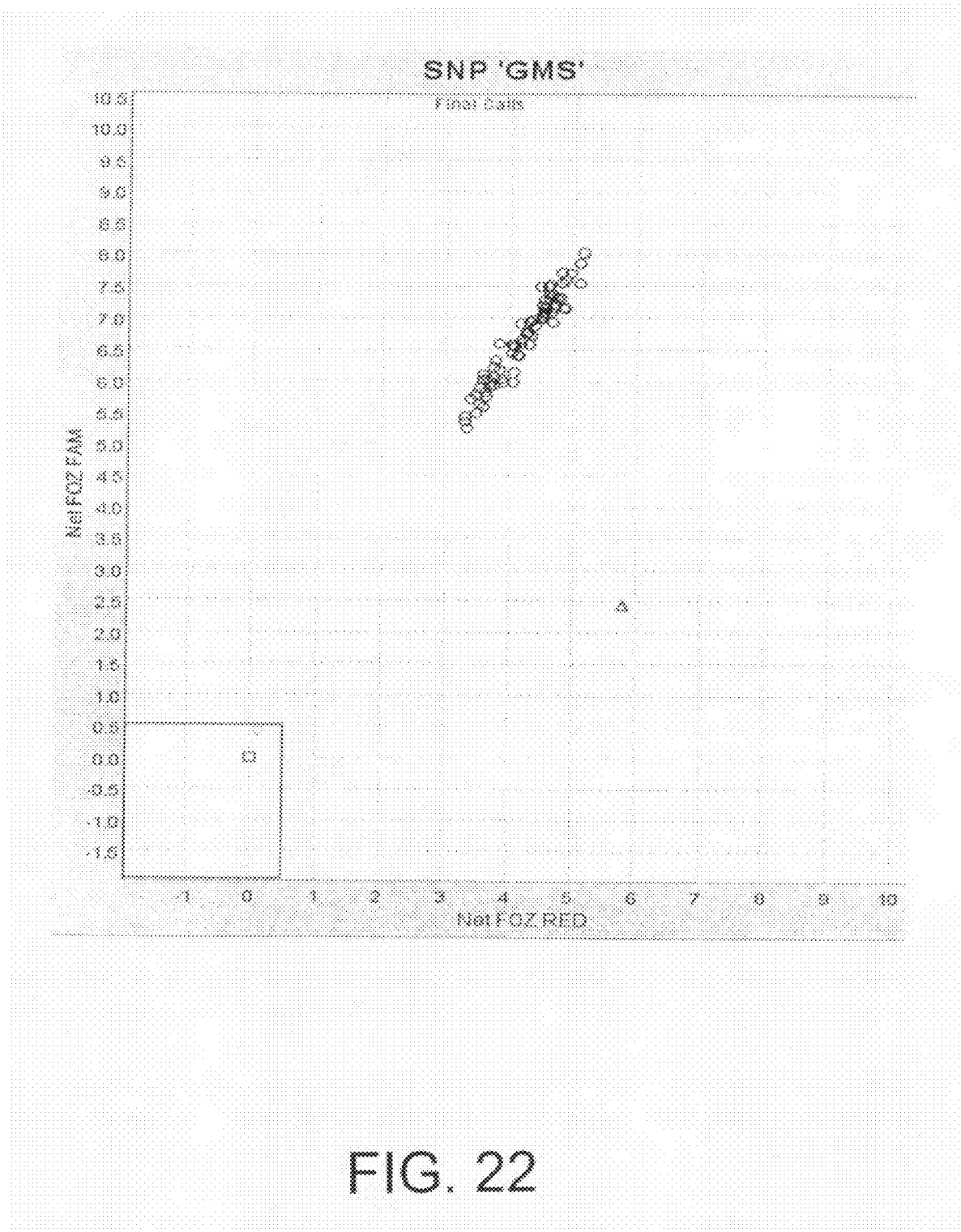

FIG. 22 shows FAM and RED scores expressed as net Fold Over Zero (FOZ) obtained after analysing pepper root border cell DNA extracts using the GMS-probe set. For each DNA sample the RED signal is plotted on the X-axis whereas the FAM signal is plotted on the Y-axis. The heterozygous signals are plotted in blue whereas the homozygous signals of control samples are plotted in red and green symbols in the graph.

Figure 23:
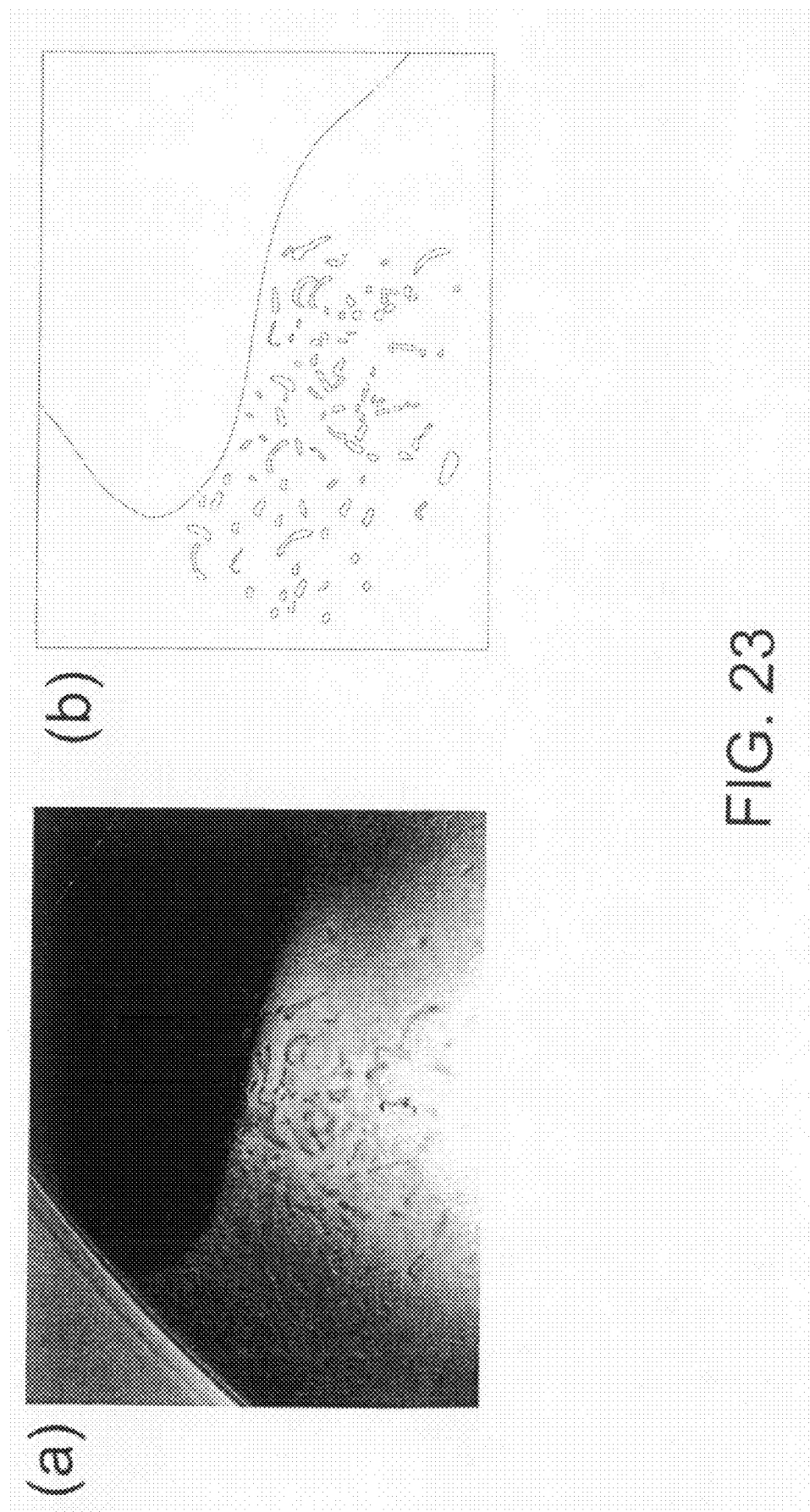

FIG. 23(a) shows a root tip of maize shedding root border cells into the liquid medium; FIG. 23(b) shows a schematic depicting the image of FIG. 23(a).

Figure 24:
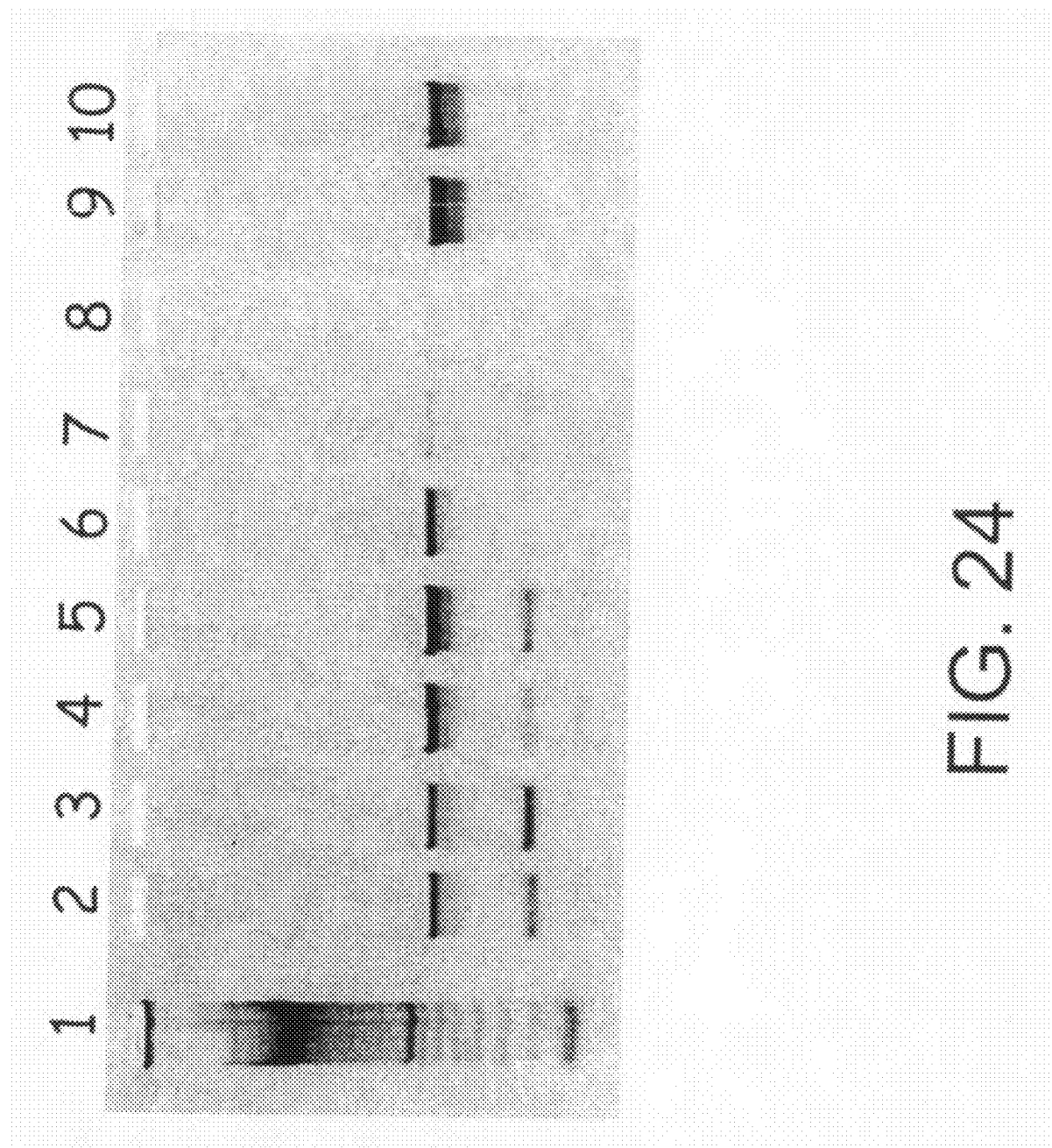

FIG. 24 shows ethidium bromide stained agarose gel showing the bands obtained by PCR analysis of the cell wall invertase gene Incw1 of different DNA samples of maize generated by the DNA extraction procedure according to this invention.

Lane 1: Size marker.

Lane 2 to 7: DNA from maize root border cells.

Lane 8: negative control, water.

Lane 9 to 10: positive control, DNA extracted from maize leaf discs.

Figure 25:
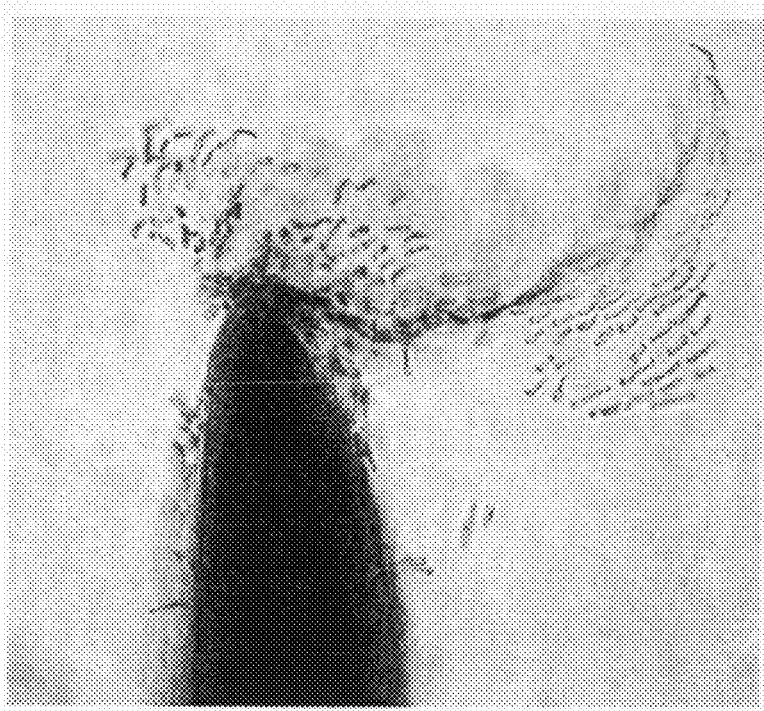
Figure 25:
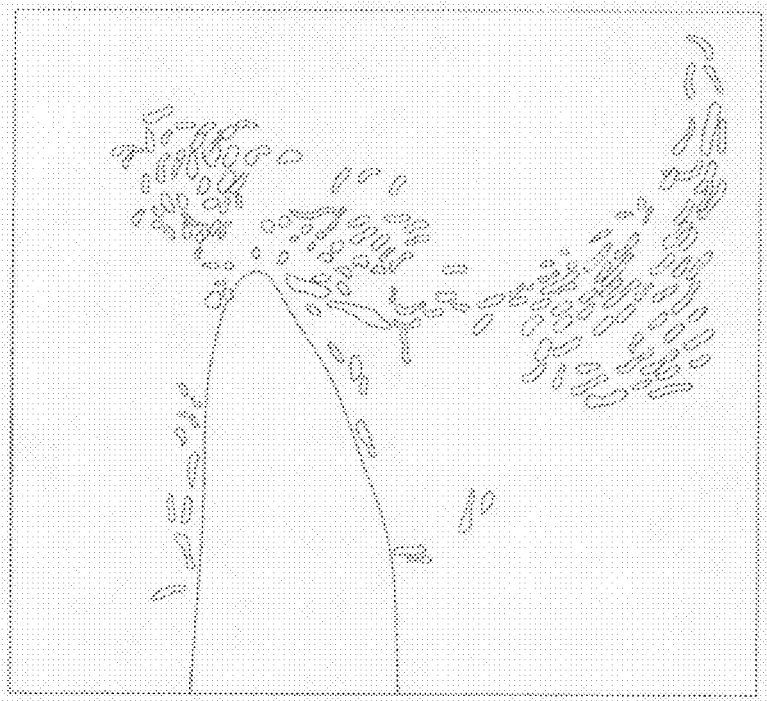

FIG. 25(a) shows a root tip of endive shedding root border cells into the liquid medium; FIG. 25(b) shows a schematic depicting the image of FIG. 25(a).

Figure 26:
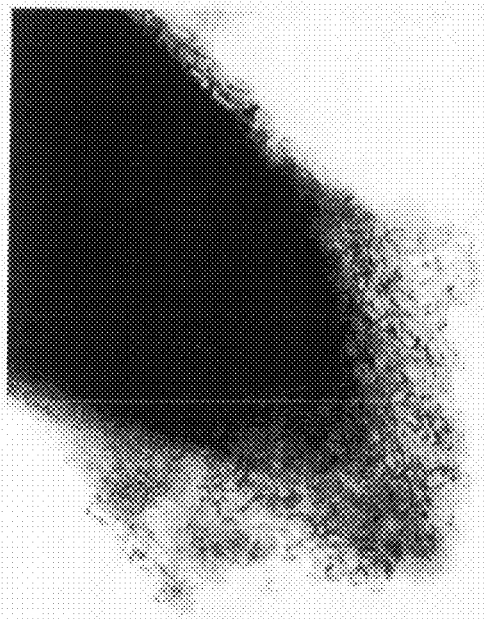
Figure 26:
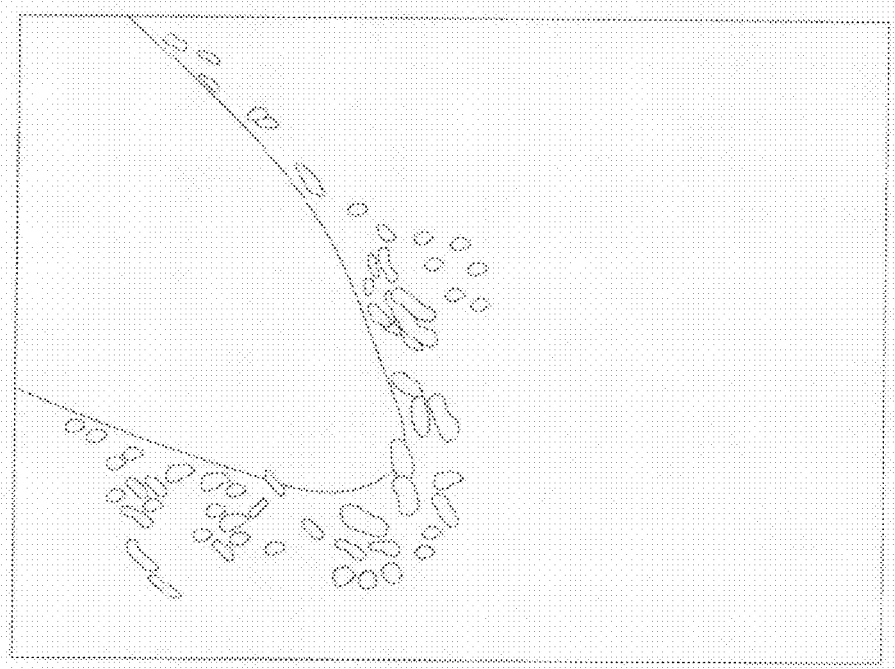

FIG. 26(a) shows a root tip of carrot shedding root border cells into the liquid medium; FIG. 26(b) shows a schematic depicting the image of FIG. 26(a).

DETAILED DESCRIPTION

Large scale sequencing efforts have provided full genomic sequences of model plant species like *Arabidopsis thaliana* and crop species like rice. Moreover, large numbers of cDNA fragments or ESTs have been sequenced originating from different tissue samples derived from a large range of crop species like tomato, lettuce, cucumber, *Brassica* spp., melon, maize, etc. The current challenge is to elucidate the function of the individual genes, the regulation of their expression and their genetic interaction. In order to meet this challenge, it will be important to dispose of large series of allelic variants of each individual gene. This will provide clues as to which biochemical role a gene product plays at the cellular, organismal or higher order level and how gene products can interact.

In order to exploit information on gene function in plant breeding, the availability of a very efficient, cost effective reverse genetics technology is desirable. Reverse genetics refers to an approach in which one starts with gene sequence information for which allelic or expression variants are being produced which are subsequently functionally analysed. This terminology is opposed to forward genetics in which a phenotypic variant is used as starting material to identify the underlying allelic form of a gene.

In order to apply reverse genetics in plant breeding, knowledge of gene function is a prerequisite. Currently, *Arabidopsis thaliana* is the most extensively studied plant system in relation to gene function and results coming from *Arabidopsis* research provide a rich source of information in this respect.

Based on homology at the amino acid sequence level one can predict the function of a homologous protein of a crop species, though direct experimental evidence is ultimately required to prove the function of the gene. Genes of crop species identified on the basis of homology to genes of model species can therefore only be considered candidate genes for specific functions. Genes with similar or identical function across species can, but not necessarily do, show high levels of homology and gene functions residing in a particular model system may only partially overlap with those residing in a given crop species.

Allelic variability, which can be exploited by reverse genetics, occurs either naturally in adapted populations or can be obtained by random mutagenesis using chemical or physical mutagenic agents like e.g. ethyl methane sulphonate (ems) or x-rays, respectively. By treating plant organs, cells, pollen or seeds with such mutagenic agents, modifications will be induced at random positions in the genomic DNA which may lead to a change in gene function.

Given the rapidly increasing knowledge on gene function, the vast availability of genomic and cDNA sequences of many plant species and the availability of populations bearing natural and induced genetic variation, reverse genetics technology is of increasing significance as a research instrument to establish gene functions in a model or crop species. In addition, reverse genetics can also be regarded as a powerful technology for crop improvement in which allelic variants of genes known to be functionally involved in specific traits can efficiently be identified.

In order to perform reverse genetics in a crop species, besides a target gene, obviously populations of plants are required which contain genetic variants of the genetic loci of the given crop species. Within such populations, the genetic variation can have occurred spontaneously or can be induced by mutagens like ems. In order to obtain a population with induced mutations, one can incubate for example seeds in a solution containing different concentrations of a mutagen like ems. Ems alkylates primarily G residues of a DNA strand which during DNA replication causes pairing with T instead of C. Therefore, GC basepairs change to AT basepairs at a frequency which is determined by the effective dose of ems and the activity of the mismatch repair system of the plant.

The effective dose of ems depends on the concentration used, the seed size and other physical properties and the time of incubation of the seeds in the ems solution. The seeds which have been treated with ems are typically called M1 seeds. As a consequence of the treatment, the tissues of the M1 seeds contain random point mutations in the genomes of their cells and those present in the subpopulation of cells which will form the germline tissue will be transferred to the next generation which is called M2. Mutations or combinations thereof which are haplo-insufficient thereby causing sterility or which induce embryo lethality will not be transferred to the M2 generation.

A similar procedure as described above for the use of ems applies for other mutagenic agents as well.

In order to assess mutant M2 populations for the presence of desirable allelic variants of specific genetic loci using reverse genetics, one can take different approaches which can be distinguished on the basis of the manner chosen to harvest and store the M2 seed population. On the one hand one can harvest and store the M2 seeds as a single bulk sample whereas on the other hand one can harvest and store the M2 seeds as families which means that the M2 seeds are harvested plant by plant and stored separately.

Harvesting the M2 seeds in bulk requires much less labour input when compared to a situation in which M2 seeds are harvested separately as families. On the other hand, harvesting M2 seeds as families allows to prepare DNA extracts of a subset of the M2 seeds of each family of the population which can be used diagnostically to analyse the population. Once a mutation is identified, only the seeds of the family corresponding to the positively diagnosed sample need to be grown in a greenhouse or field in order to obtain the mutant.

In case a bulked M2 population is available, M2 plants need to be grown and sampled for DNA extraction and analysis separately which requires relatively large resource input for each screen carried out. Therefore both approaches have their specific disadvantages and a clear need in the art exists to provide solutions which can lift the disadvantages of both approaches.

When the M2 seeds have been harvested in bulk, non-destructive sampling is required to identify the individual plant containing the desired allelic variant of a specific gene. Usually this is done by growing young plants of the M2 population and sampling these plants individually by taking leaf samples and preparing DNA therefrom which is used for analysis. These leaf samples can be pooled before DNA extraction to a degree determined by the dynamic range of the mutation detection platform used. Appropriate labelling allows to trace back the subpopulations containing the desired mutation and ultimately the corresponding individual plant.

The number of M2 plants which needs to be screened depends on the frequency of mutation in the M1 plants and the number of independent cells contributing to the germlines in the plant species under investigation. In a typical experiment one should screen approximately 10.000 M2 plants when starting from a population of 5000 M1 plants to capture the induced genetic variation in case of 2 independent germinal cells/plant.

In case the M2 seeds are harvested plant by plant, the induced mutations residing in the cells contributing to the germline(s) of the M1 plants on which these seeds are harvested are segregating in the M2 family. By preparing a DNA sample from a number of individuals of an M2 family one can diagnose for the presence of mutations in a target gene without a need to re-sample the population each time. In other words, a single DNA sample can be used diagnostically for the M2 family which it represents. The individual plants containing the desired allelic variants of a specific gene can be obtained by raising individuals of only those M2 families which were positively diagnosed for the desired mutations.

Although this approach is relatively efficient once the M2 families are established, setting up such family-based system is labour intensive as it requires the individual harvesting and processing of seed grown on M1 plants as well as setting up a DNA library as a representative reflection of the genetic variation of the population. It is estimated that the processing of 5000 M2 families requires the input of at least 250 man hours. Importantly, in case the desired mutation is not present in the population one has to repeat the whole exercise.

In order to detect mutations in the DNA isolated from (pooled) plant samples the person skilled in the art disposes of a number of established technologies. Tilling (targeting induced local lesions in genomes) is based on the specific cleavage by Cell of labelled heteroduplex DNA fragments generated by PCR at the position of the mismatch. The digested samples are analysed by denaturing gel electrophoresis (e.g. on a Licor system) and the presence of digested PCR fragments indicate the presence of DNA polymorphisms in the original DNA pool (Colbert, T. et al (2001) Plant Physiology 126, 480-484).

Denaturing high-performance liquid chromatography (dHPLC) can be applied on pooled DNA samples as well. Similar to the tilling procedure, the presence of a mutation leads to the formation of heteroduplex molecules which run faster through a dHPLC column as compared to the homoduplex molecules allowing the detection of mutations in pooled samples (McCallum, C. et al. (2000) Nature Biotechnology 18, 455-457).

When fast neutrons are used as mutagenic agents, small deletions are being created in the genome at random positions. This allows amplification of mutated loci, which by consequence of the deletion have been reduced in size, by PCR. As this PCR reaction is specific for the mutated locus, a very high level of sample pooling becomes feasible. On the other hand, this method only applies for those mutations which allow specific PCR reactions to be designed like for loci containing deletions (Song, X. et al (2001) The Plant Journal 27, 235-242).

It is clear to the person skilled in the art that basically any available nucleic acid analysis technology can be applied to detect polymorphisms between DNA samples. Even direct sequencing of individual samples can be applied. In an industrial setting the platform of choice will largely be determined by its robustness and cost per data point.

With the availability of a variety of induced mutation detection technologies and the advances in automation and miniaturisation, cost per data point will be reduced to relatively low levels when compared to cost involved in preparing M2 populations and representative DNA templates.

Therefore, improvements of reverse genetics of plants are better to be realised in the area of preparing mutant populations and their representative DNA samples rather than in the detection of the induced polymorphisms. Such improvements are provided by the current invention.

In either case, i.e. applying reverse genetics on the basis of M2 bulk populations or M2 families, substantial labour input will be required either during the screen or upfront, respectively. This severely limits the cost-effective applicability of reverse genetic approaches in crop species.

The DNA isolation method of the invention can also be used for the selection of plants during plant breeding. Progress in plant breeding is achieved through crossing and selection of plants out of a progeny population. Traditionally, the selection occurs at the level of the plant phenotype manifesting under specific growing conditions. For example, plants are selected on the basis of their fruit and leaf colour or shape, their resistance to pathogens, their productivity or other traits or combinations thereof.

With the advent of molecular marker technologies, selection for specific traits can be carried out at the level of the DNA. Technologies have been developed which allow the identification and detection of marker alleles which are genetically tightly linked to an allelic form of a gene which is causing the expression of a certain phenotype. In the ideal situation the marker allele and the allelic form of the gene responsible for a certain trait are identical. In such case the marker allele and the trait allele cannot be uncoupled by genetic recombination.

The use of marker alleles for indirect selection of traits has a number of clear advantages which improve the efficiency of the selection process. The marker based selection is independent of the developmental stage of a plant and the environment. This allows for example to select for fruit characteristics at the seedling stage or to select for cold tolerance at room temperature. Currently, indirect selection using marker alleles is applied extensively in modern plant breeding. Most advanced is the application of markers to detect qualitative traits i.e. traits for which the phenotypic variation within the germplasm is determined by allelic forms of a single gene.

For example, resistances to specific strains of a pathogen are often determined by the presence of dominant R genes which code for receptors which detect the presence or activity of a virulence factor of the pathogen. Although the expression of the resistance phenotype involves many loci, the genetic variation which resides in the germplasm and which explains the phenotypic value is usually determined by a single R-gene locus.

Many traits however are quantitative or continuous which means that many genes can contribute to the phenotypic value of the trait which often is affected by the environmental conditions. Such traits are for example plant height, flowering time or yield potential. Moreover, the individual genes underlying the complex trait can interact epistatically, which complicates the analysis of their inheritance.

With the availability of high density genetic maps and powerful statistical tools the detection of loci involved in the expression of these quantitative traits (QTL) is currently feasible. It can therefore be anticipated that the number of (complex) traits that can be detected using molecular markers will significantly increase in the near future.

In order to apply indirect selection, currently one has to germinate the seeds of the population from which individual plants need to be selected in a greenhouse to a stage at which a tissue sample can be taken for DNA extraction. Depending on the crop species this can be carried out at the seedling stage or young plant stage. After performing the DNA analysis, selection of the plants can take place. Obviously, such procedure takes time, space and labour which consumes a relative large part of the total resources needed to carry out molecular marker based indirect selection.

Technology which increases the efficiency of the procedure to obtain a DNA extract of sufficient quality and quantity to perform DNA analyses can significantly reduce the cost involved in molecular marker based indirect selection. Such technology is provided by the current invention.

The present invention provides a novel method to isolate DNA from plants in a highly efficient, non-destructive manner. This method can for example be applied to significantly improve the overall efficiency of reverse genetics as well as indirect selection technologies.

The DNA isolation method can be effectively applied at a very early stage of plant development i.e. at the stage of radicle emergence from the imbibed seed and, importantly, does not require any tissue sampling through punching or cutting and the like.

When seeds are placed under the appropriate conditions of moisture, light and temperature, water will be taken up and germination will be initiated. Usually, the first visible sign of germination is the emergence of the radicle or root tip. While growing, the zone behind the root tip discards viable cells called root border cells into the environment (Hawes, M. et al. (1998) Annu. Rev. Phytopathol. 36, 311-327).

Although the function of the root border cells is not entirely clear, the current hypothesis is that these cells protect the plant against toxic elements like aluminium or pathogenic micro-organisms by the formation of a diffuse boundary between the plant body and the soil in which it grows. In addition, root border cells may have a function in attracting beneficial microorganisms or to establishing mycorrhiza. Root border cells may therefore be very important in controlling the micro-environment of the root system.

When seeds are germinated in vitro e.g. in water, root border cells are produced as well and remain loosely attached to the root surface. Upon gentle agitation, the root border cells are released from the root surface, disperse into the liquid and can be harvested. According to the invention, it was surprisingly found that these root border cells can serve as source of DNA for diagnostic purposes. Most, if not all, crop species are known to produce root border cells implying the general applicability of the current invention.

When seeds are germinated in water to a stage in which the root has emerged to about 1-2 cm, the water contains sufficient cell material to perform a standard DNA extraction procedure providing sufficient DNA for further analysis by PCR or other DNA analysis technologies.

According to the invention it was also found that roots of in vitro plants produce root border cells. Such root border cells that do not originate from the root tip of a germinating seed or seedling but from adventitious roots on tissue culture material can thus also be used to isolate DNA therefrom.

Figure 18:
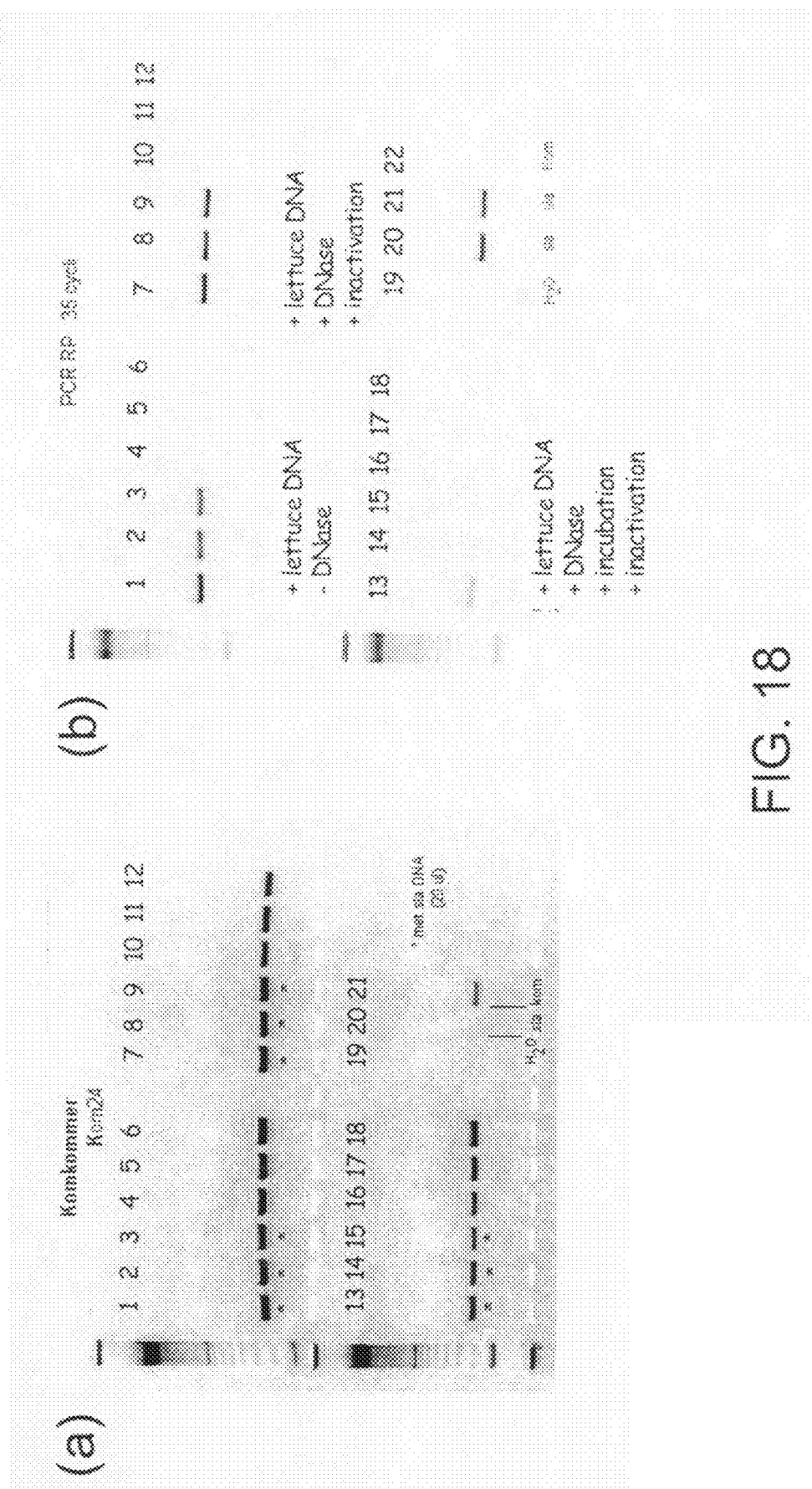
FIG. 18(a) shows ethidium bromide stained agarose gel showing PCR analysis using the cucumber kom24 specific primer combination.
FIG. 18(b) shows ethedium bromide stained agarose gel showing PCR analysis using the lettuce specific RP primer combination. Lanes 1-18 contain DNA isolated from cucumber root exudates which were subjected to the following treatments: To the root exudates analysed in lanes 1-3, 7-9 and 13-15 lettuce genomic DNA was added. To the samples of lanes 1-6, no DNase was added. To the samples of lanes 7-12, DNase was added and immediately inactivated by incubation for 5 minutes at 65EC. To the lanes 13-18, DNase was added followed by incubation for 30 minutes at 37EC and subsequent inactivation. As controls in panel A, water (lane 19) lettuce DNA (lane 20) and cucumber DNA (lane 21) was used. As controls in panel B, water (lane 19) lettuce DNA (lane 20 and 21) and cucumber DNA (lane 22) was used.

When a root border cell suspension is treated during one hour with an effective concentration of DNase, a signal can still be obtained after the inactivation of the DNase and subsequent extraction of the DNA (FIG. 18). This corroborates the notion that the DNA which is obtained from the root exudate is indeed derived from DNase resistant structures such as the root border cells.

The amount of DNA which can be obtained is sufficient to carry out many analyses, especially when using sensitive fluorescence-based detection technologies like Invader™ or Invader Plus™ (Third Wave Technologies).

Seeds of most, if not all, crop species which are of sufficient physical quality germinate within a few days in water. It was observed that during this very early stage root border cells are formed. The DNA extraction and analysis can therefore surprisingly be completed within a few days starting from the dry seeds. As the germinated seeds remain viable for at least 2 weeks in vitro, the time and place normally required to grow plants in a greenhouse as well as the labour required to harvest tissue samples can be largely omitted.

The same applies to tissue culture roots. The root border cells can be isolated from the medium and the in vitro plant can continue growing. The analysis can be performed in a very early stage of plant development.

It is further shown according to the invention that seeds from bulked M2 populations can be germinated in small pools of 2-5 seeds which provides pooled DNA samples which can be analysed on detection platforms which have a dynamic range of detecting one mutant allele in a pool containing 3-9 times the amount of wild-type alleles.

Pooling can also be done at the level of root border cell harvesting, DNA extracts or the PCR product. The actual pooling strategy taken will depend on the technicalities of different processes including germination behaviour of seeds in liquid and root border cell production which may differ from crop species to crop species as well as the dynamic range of the detection platform in which an optimum can be found in terms of cost per plant.

With respect to the efficiency in terms of resource input of reverse genetics or indirect selection approaches using either bulked M2 seeds or M2 families or breeding populations, the method according to the present invention has a number of important implications. As the non-destructive DNA extraction procedure using root border cells can be carried out very early after germination of seeds in vitro, and given the fact that the seedlings remain viable for at least several weeks in vitro, the reverse genetics approach in which bulked M2 populations are used or the indirect selection approach, no longer requires greenhouse time and space as well as the labour-intensive preparation of plant samples like leaf discs. This means that the alternative for working with M2 bulk populations i.e. working through M2 families which required significant upfront input of resources is not required anymore.

In addition, the indirect selection procedure during breeding does not require growing plant material in a greenhouse which would not be selected. Therefore, with the present invention, any population at hand which needs to be assessed for allelic variability at specific loci can be screened with unprecedented efficiency and flexibility when compared with reverse genetics or indirect selection procedures currently known in the art.

The DNA isolation method for plants of this invention is applicable in the broadest sense. In the present application reference is made to several situations in which an efficient non-destructive method for isolating DNA is advantageous. These examples are not intended to be limiting. It will be clear to the skilled person that the method can be used for any DNA isolation and is equally applicable in other situations not mentioned here.

The present invention will be further illustrated in the non-limiting Examples that follow.

EXAMPLES

Example 1

DNA Extraction and Analysis from Root Border Cells of Cucumber

Cucumber seeds are germinated in 100 Fl water (milliQ) at 26EC. Depending on the objective, different formats can be used like a 12×8 Micronic™ microtubes format which allows easy transfer of samples to a 96-well microtiter plate for further treatments. At a stage where the emerging root has a length of approximately 1.5 cm, which depending on the variety and quality of the seed occurs after approximately 18 hours, the tubes containing the germinated seeds are gently shaken by vortexing during 15 seconds to release the root border cells from the root. Evaluation by light microscopy clearly showed the presence of root border cells of cucumber in the medium as shown in FIGS. 1(a) and 1(b) and FIGS. 2(a) and 2(b).

The main root and root hairs are not damaged by this procedure. The liquid containing the root border cells is used to carry out DNA extraction (Plant DNA isolation kit, Agowa GmbH in combination with King Fisher™ robotics, Thermo Labsystems) by adding 100 Fl lysis buffer (Agowa). The mixture is incubated during 10 minutes at 55EC. Subsequently 300 Fl of DNA binding buffer (Agowa) is added and the mixture is centrifuged during 5 minutes at 3000 rpm. Subsequently, 15 Fl of a King Fisher particle suspension (Agowa Magnetic Particles (Suspension BLM)) is added to the supernatant.

After the bound DNA is eluted from the particles using 120 Fl elution buffer (10 mM Tris-HCl buffer pH=7.6) the DNA is ready for analysis. For cucumber, a random molecular marker residing in the genome named "kom20" was chosen to analyse the DNA obtained from the root border cell based DNA extracts.

Figure 1:
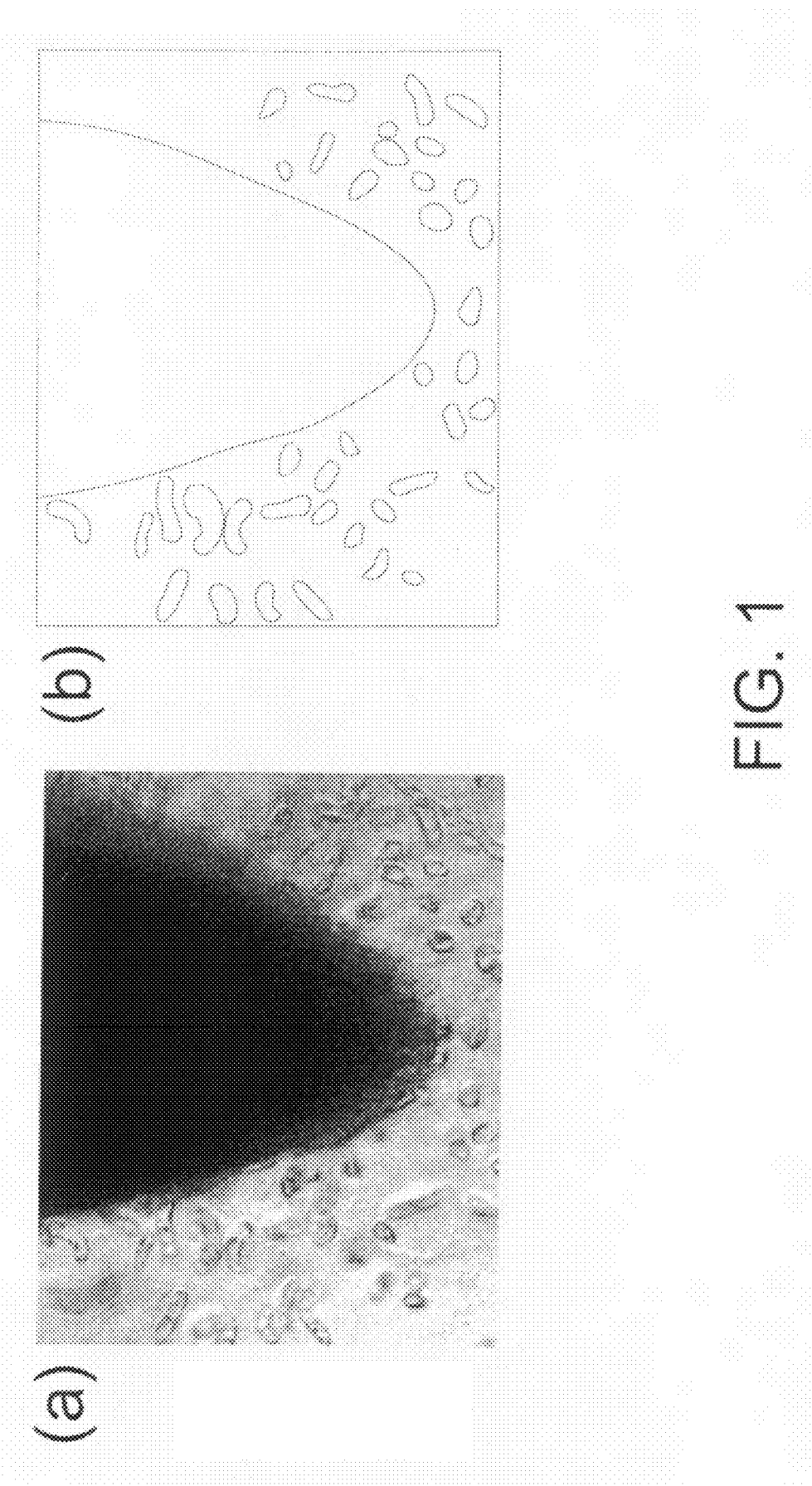
FIG. 1(a) shows an image under white light of a root tip of cucumber shedding root border cells into the liquid medium.
FIG. 1(b) shows a schematic depicting the image of FIG. 1(a).
Figure 2:
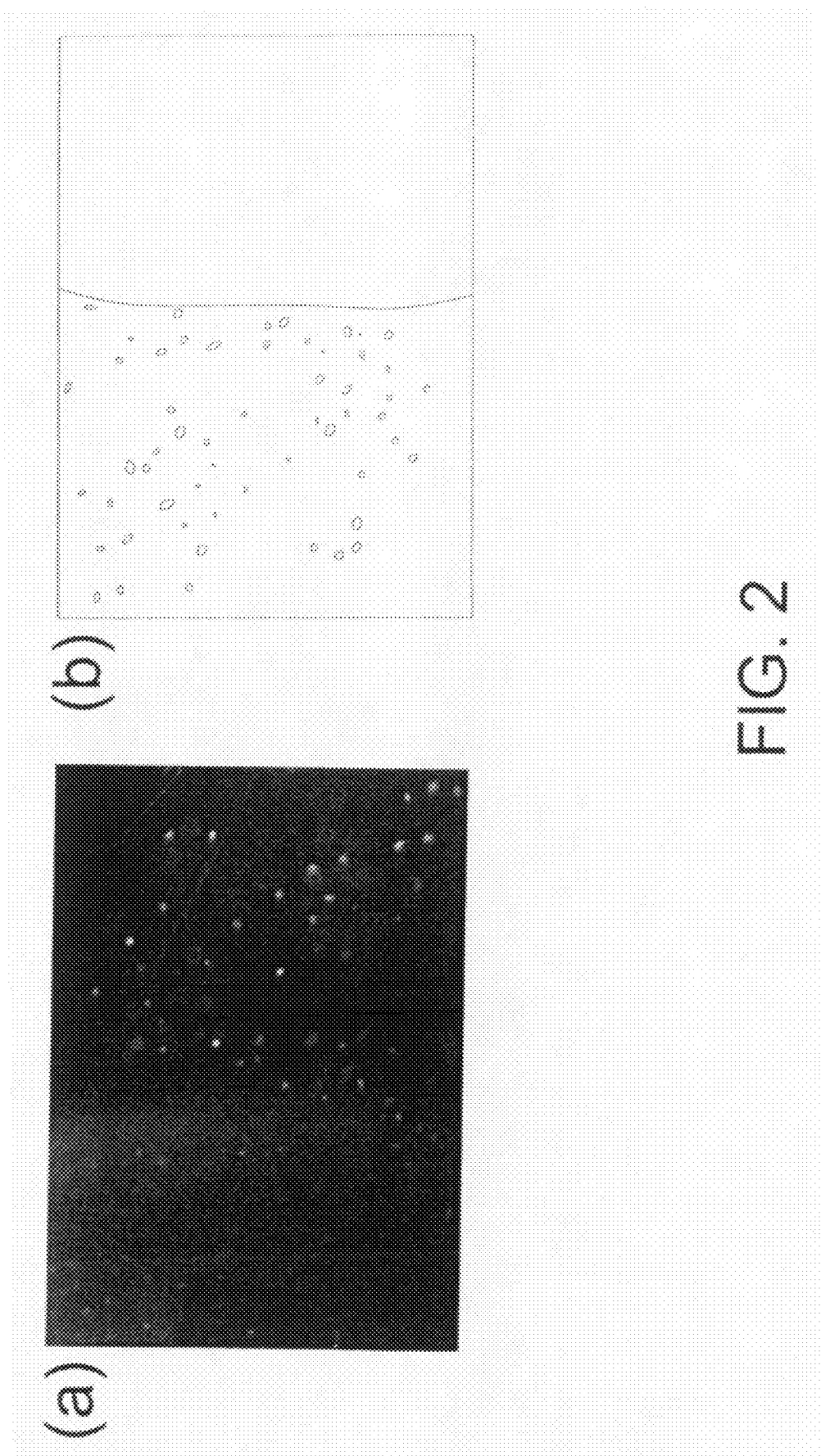
FIG. 2(a) shows the nuclei of root border cells under fluorescent light after DAPI staining.
FIG. 2(b) shows a schematic depicting the image of FIG. 2(a).
Figure 3:
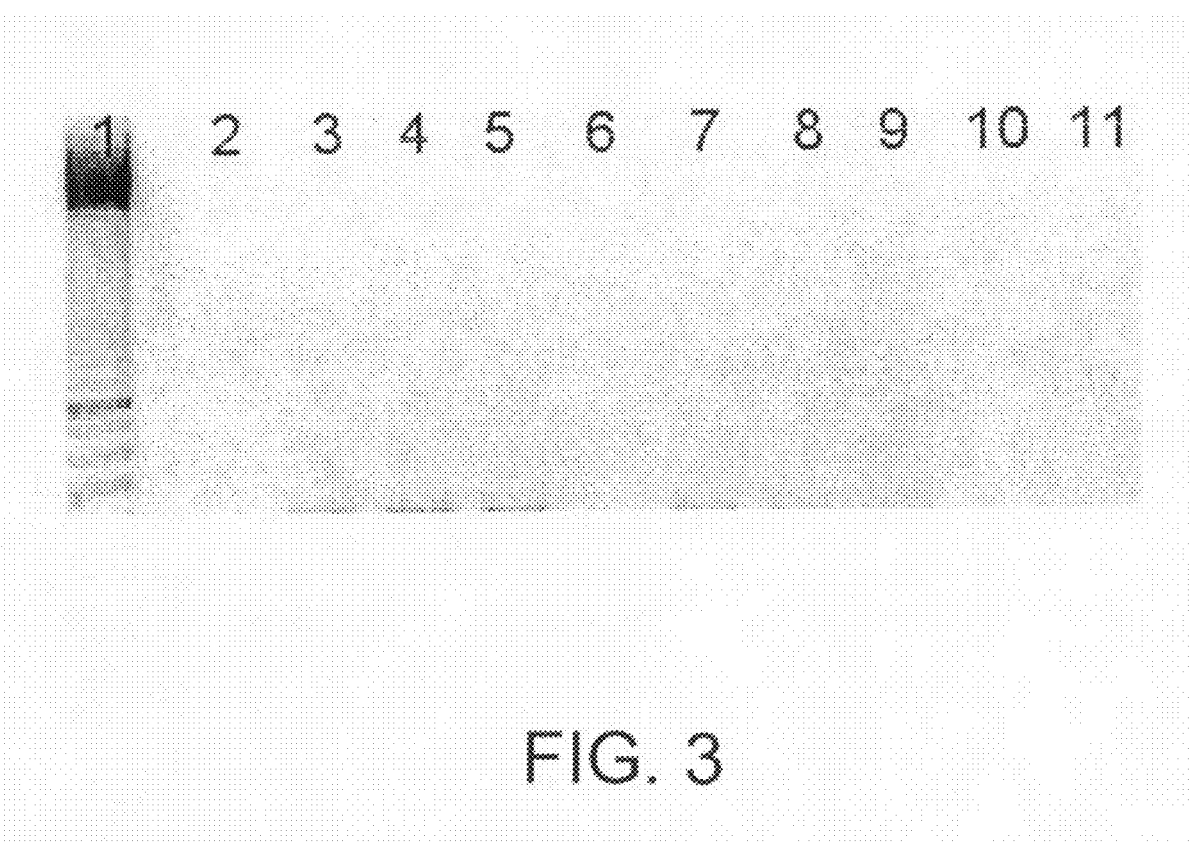
FIG. 3 shows ethidium bromide stained agarose gel showing the bands obtained by PCR analysis followed by MspI digestion of the kom20 marker locus of different DNA samples of cucumber generated by the DNA extraction procedure according to this invention.
Lane 1: size marker,
Lanes 2 to 11: 10 individual cucumber root border cell preparations,
Lane 12: negative control: lettuce root border cell preparation,
Lane 13: negative control: water,
Lane 14: positive control: cucumber leaf disc.

The population used in this example segregates either heterozygous or homozygous for one of the alleles of the kom20 marker. PCR was carried out using 5 Fl of the total amount of the DNA extract obtained. The PCR reaction is anticipated to result in a fragment of 372 bp when analysed on an agarose gel. Digestion of the kom20 PCR fragment using the restriction enzyme MspI discriminates between the two alleles of this marker locus in the population used for the experiment described in this example. When the recognition site for the restriction enzyme is present in the PCR product, digestion with MspI results in fragments of 279 and 93 bp. The result of the analysis is shown in FIG. 3.

Figure 4:
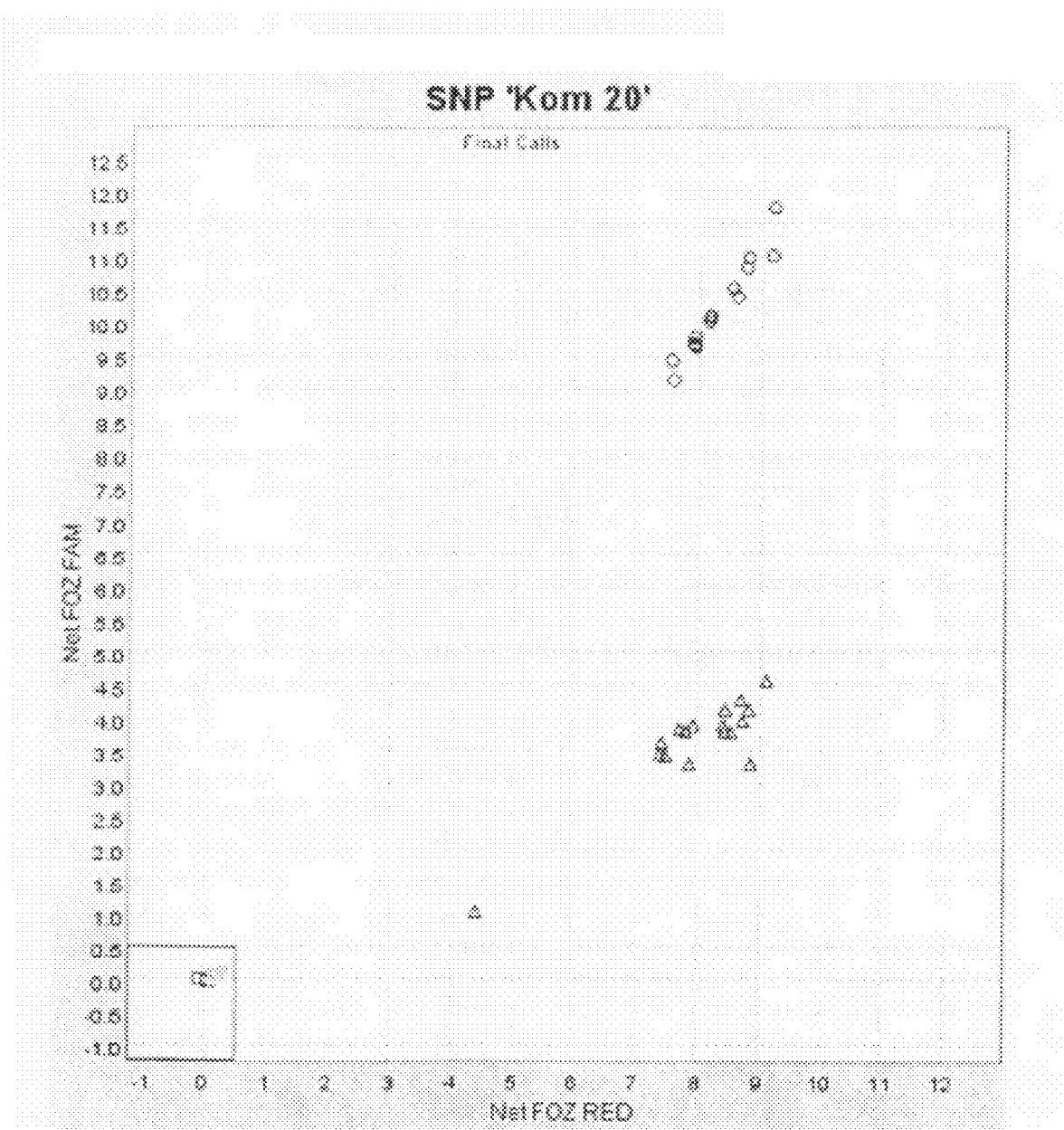
FIG. 4 shows FAM and RED scores expressed as net Fold Over Zero (FOZ) obtained after analysing cucumber root border cell DNA extracts using the kom20-probe set. For each DNA sample the RED signal is plotted on the X-axis whereas the FAM signal is plotted on the Y-axis.
Figure 5:
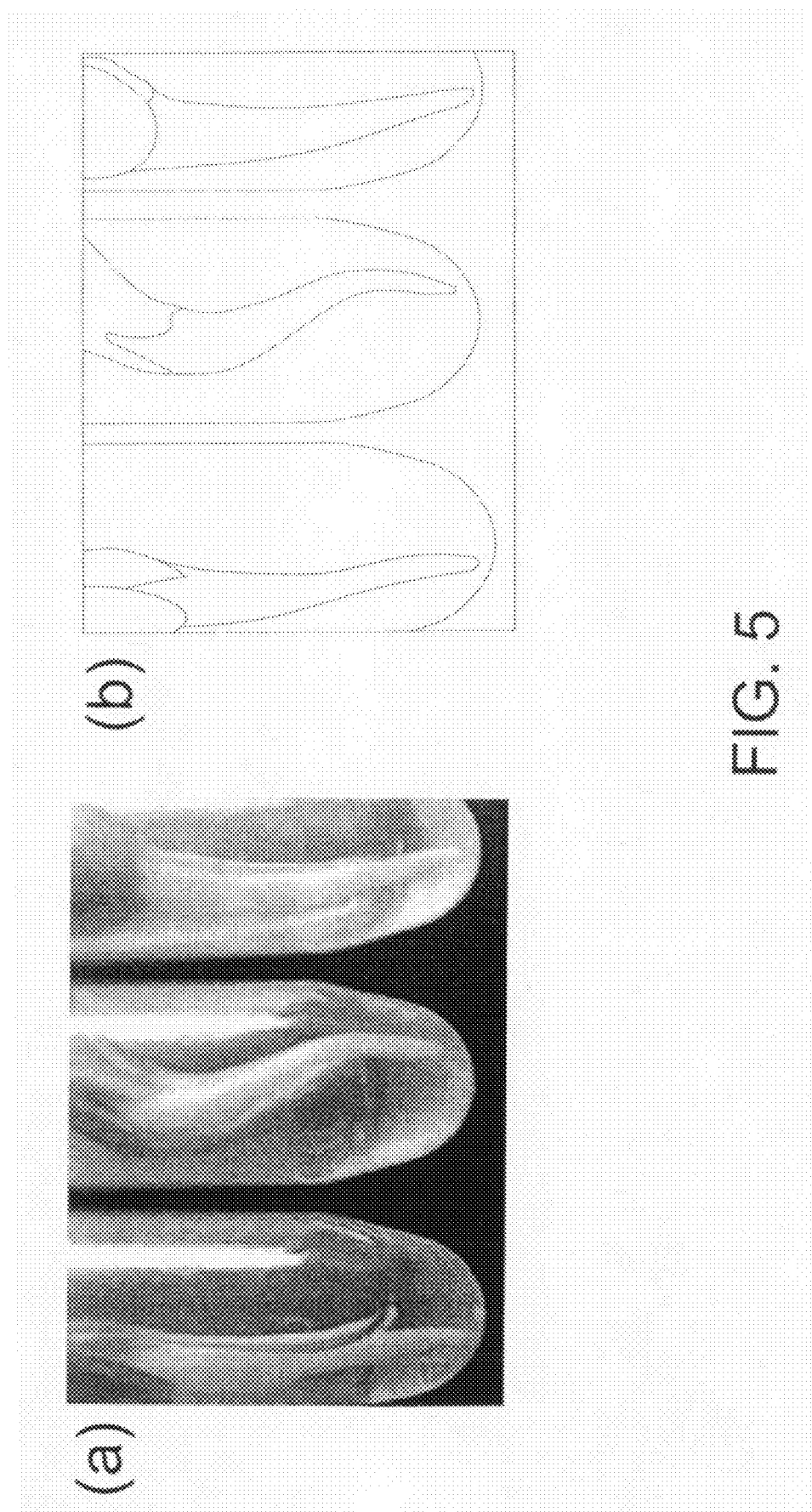
FIG. 5(a) shows the germinated melon seeds with their root tip in liquid medium.
FIG. 5(b) shows a schematic depicting the image of FIG. 5(a).
Figure 6:
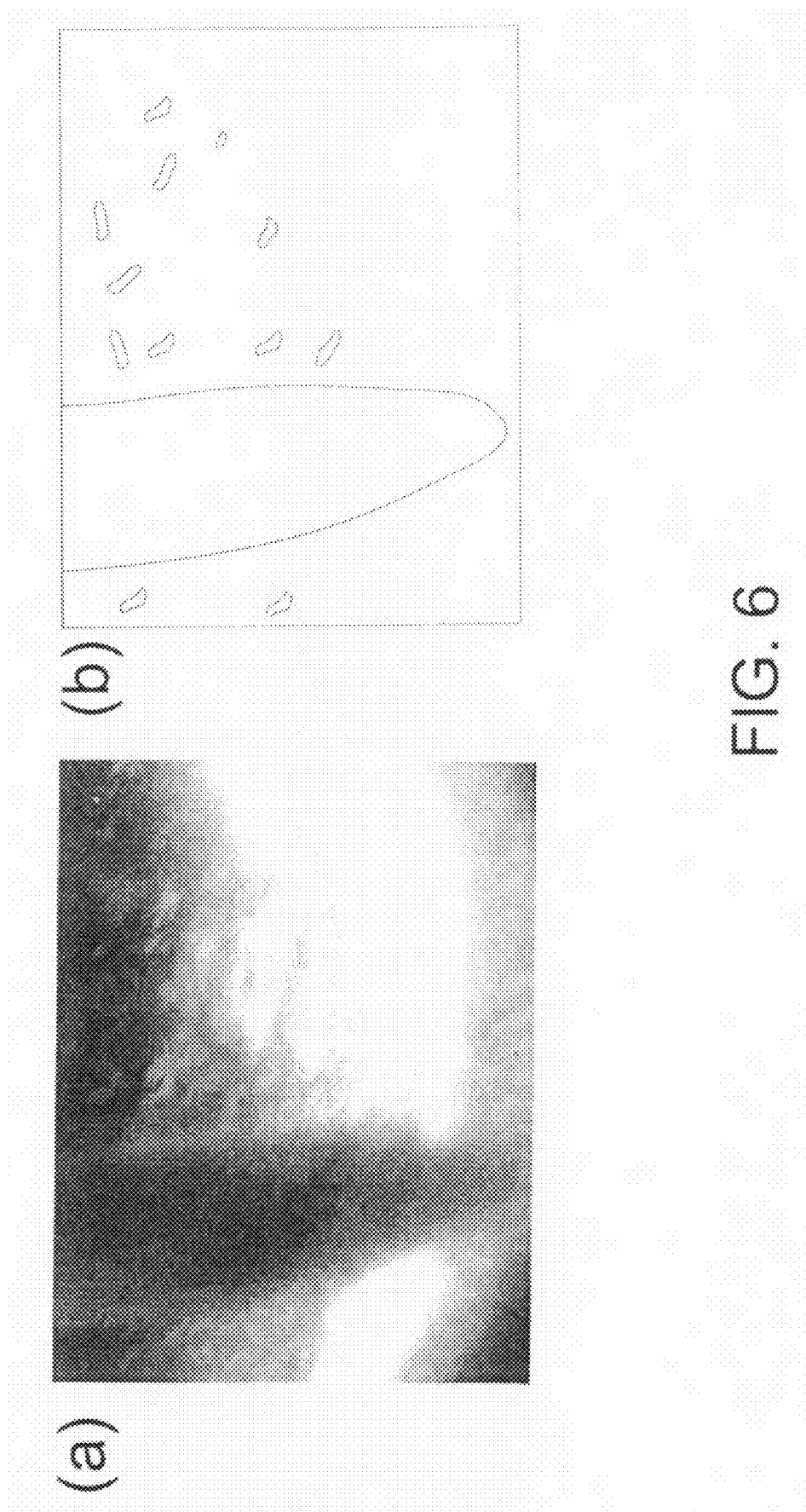
FIG. 6(a) shows the shedded root border cells coming from the root.
FIG. 6(b) shows a schematic depicting the image of FIG. 6(a).

To confirm this result, the DNA preparations were analysed using a kom20-specific fluorescent probe set (Invader™) which generates a specific fluorescent signal (expressed as net Fold Over Zero or FOZ) for each of the kom20 alleles (FAM or RED). It is therefore expected that DNA preparations obtained according to the current invention from the individuals of the segregating population analysed using kom20-probes will generate fluorescent signals diagnostic for either heterozygocity of the marker alleles (plotted on the diagonal, RED+FAM signal) or fluorescent signals diagnostic for homozygocity of one of the marker alleles (for this particular case labelled RED and plotted on the X-axis). The result of the analysis is shown in FIG. 4 and confirms this expectation.

The kom20 genotypic scores obtained using either the PCR/MspI or the fluorescence based analysis of the population were found to be consistent for each plant analysed. Therefore, the results demonstrate that the amount of DNA isolated according to the procedure which is the subject of this invention is adequate to carry out DNA marker analysis using PCR in combination with agarose gel electrophoresis or the fluorescence-based probe system as detection platforms. It can further be concluded that the marker calls are derived from DNA from the hybrid tissues residing in the seeds and not from maternal tissue as the markers used are segregating which is not the case in the maternal line used to create the hybrid seeds used for this analysis.

To confirm the data obtained using the DNA isolation procedure according to this invention, the germinated seeds were grown in the greenhouse and leaf samples were taken and analysed for the kom20 marker using PCR/MspI. The data obtained using leaf DNA were shown to be consistent with the data obtained using DNA from root border cell DNA extracts. This demonstrates that the marker data which are generated through root border cell DNA extracts are representative for an established plant which is grown from the emerging seedling.

In order to determine the amount of assays which can be carried out per DNA extract, a dilution series of the DNA extract was assayed using 5 fluorescence-based assays in duplo which detect 5 different, random marker loci. It was found that each DNA extract could be diluted at least 20-fold without losing any of the signals of the different assays. As each extract is produced in a volume of 100 Fl, and 5 Fl is used per assay, a total of 400 assays can be run per DNA extract per isolation. In addition, for cucumber at least 2 rounds of root border cell harvest and DNA isolation can be performed per seedling which means that a total of 800 assays can be carried out per seedling using root border cell DNA extracts.

When the germinated seeds which have been used as a source of root border cell DNA are stored at 4EC, the cucumber seedlings remain viable for at least 3 weeks. This implies that the seedlings have a sufficient level of viability to be transferred to a greenhouse after the DNA analysis has been completed.

Therefore, only those plants which have the desired molecular marker scores need to be transferred to a greenhouse and plants which do not have the desired molecular marker scores can be discarded at a very early in vitro phase. This can result in considerable cost savings.

Example 2

DNA Extraction and Analysis from Root Border Cells of Melon

Melon seeds of a selfed progeny of hybrid variety called Danubio are germinated in 100 Fl water (milliQ) at 26EC. The procedure which is used to isolate DNA from melon is comparable to the procedure described for cucumber in Example 1 of this application. FIGS. 5(a) and 5(b) and FIGS. 6(a) and 6(b) show the presence of root border cells in liquid medium containing melon seedlings.

In order to investigate if the procedure results in sufficient DNA to detect a maker allele using PCR, 5 Fl of the DNA extract was used to carry out a PCR reaction using a primer combination specific for the marker allele ml11k19. The PCR reaction is anticipated to result in a fragment of 342 bp. The result of this analysis is shown in FIG. 7.

Figure 7:
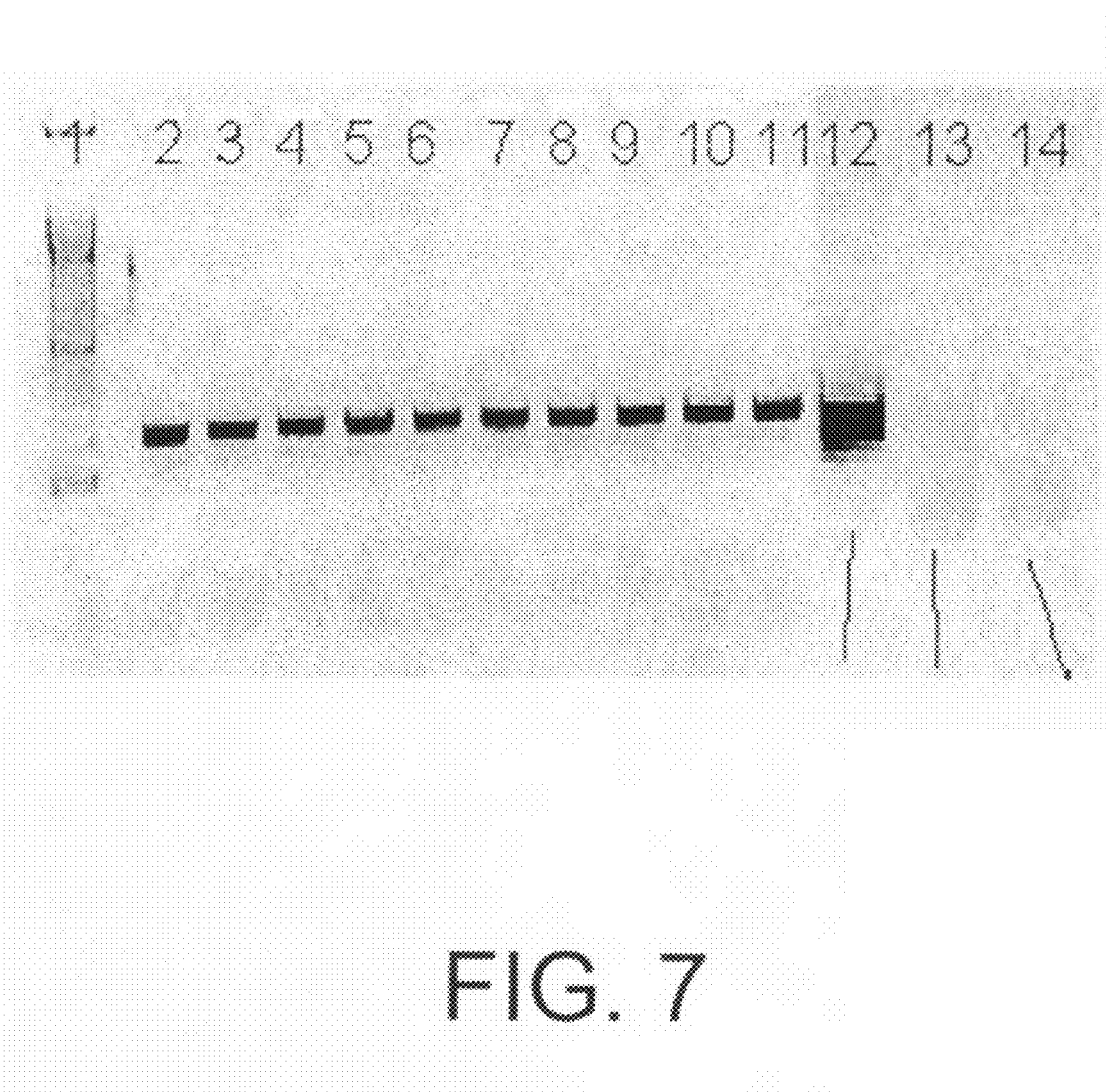
FIG. 7 shows ethidium bromide stained agarose gel showing the bands obtained by PCR analysis of the ml11k19 marker locus of different DNA samples of melon generated by the DNA extraction procedure according to this invention.
Lane 1: size marker,
Lanes 2 to 11: 10 individual melon root border cell preparations,
Lane 12: DNA from melon leaf disc,
Lane 13: negative control, lettuce root border cell preparation,
Lane 14: negative control, water.
Figure 8:
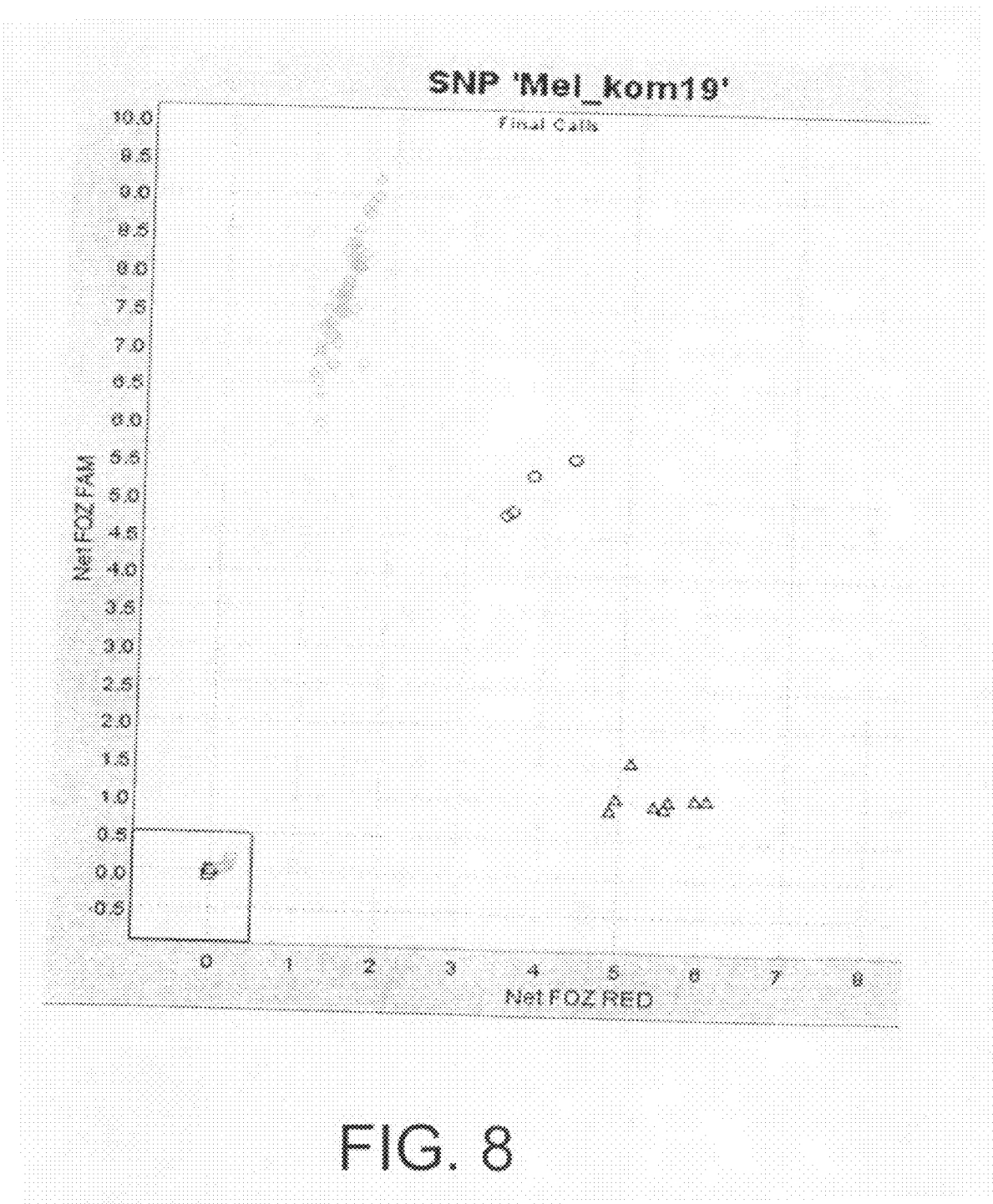
FIG. 8 shows FAM and RED scores expressed as net Fold Over Zero (FOZ) obtained after analysing melon root border cell DNA extracts using the ml 11k19 probe set. For each DNA sample the RED signal is plotted on the X-axis whereas the FAM signal is plotted on the Y-axis.

The result shown in FIG. 7 demonstrates that sufficient DNA has been obtained in order to generate the expected DNA fragment by PCR. To demonstrate that the fragment is indeed derived from the embryo, a fluorescence based ml11k19-assay was carried out which detects both alleles present in the original hybrid and which are anticipated to segregate in the seeds used in this analysis. The results of this experiment are shown in FIG. 8.

The result clearly demonstrates segregation of the marker allele ml11k19 into three classes: homozygous A (FAM signal), homozygous B (RED signal) and heterozygous which shows that the DNA is of embryonic origin.

Example 3

DNA Extraction and Analysis from Root Border Cells of Tomato

Figure 9:
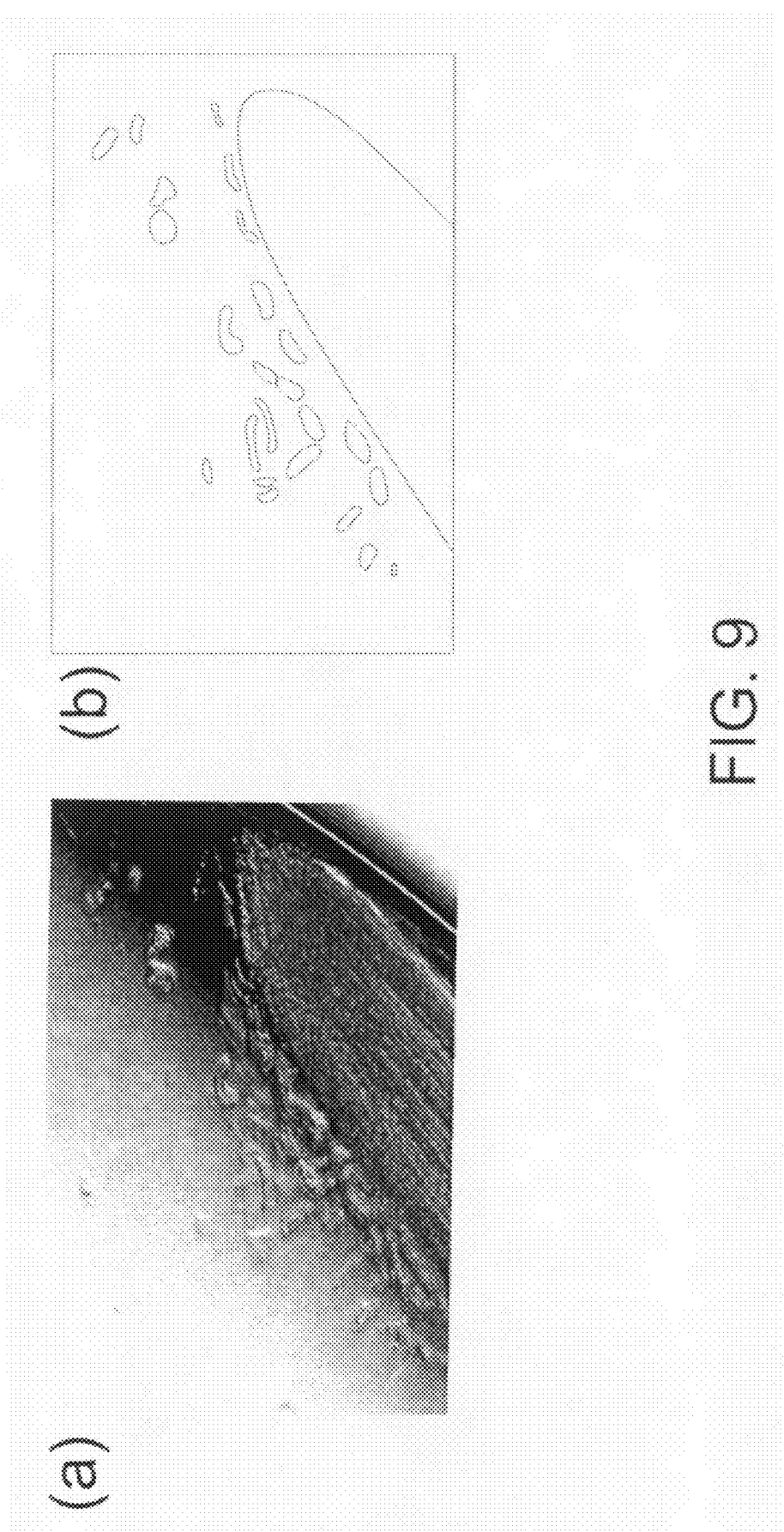
FIG. 9(a) shows a root tip of tomato shedding root border cells into the liquid medium.
FIG. 9(b) shows a schematic depicting the image of FIG. 9(a).

Tomato seed were germinated in 50 Fl water (milliQ) at 26EC and when the emerging roots had a length of on average 1.0 cm, DNA was extracted according to Example 1 of this application. Analysis by light microscopy clearly showed the presence of root border cells of tomato in the medium as shown in FIGS. 9(a) and 9(b).

Figure 10:
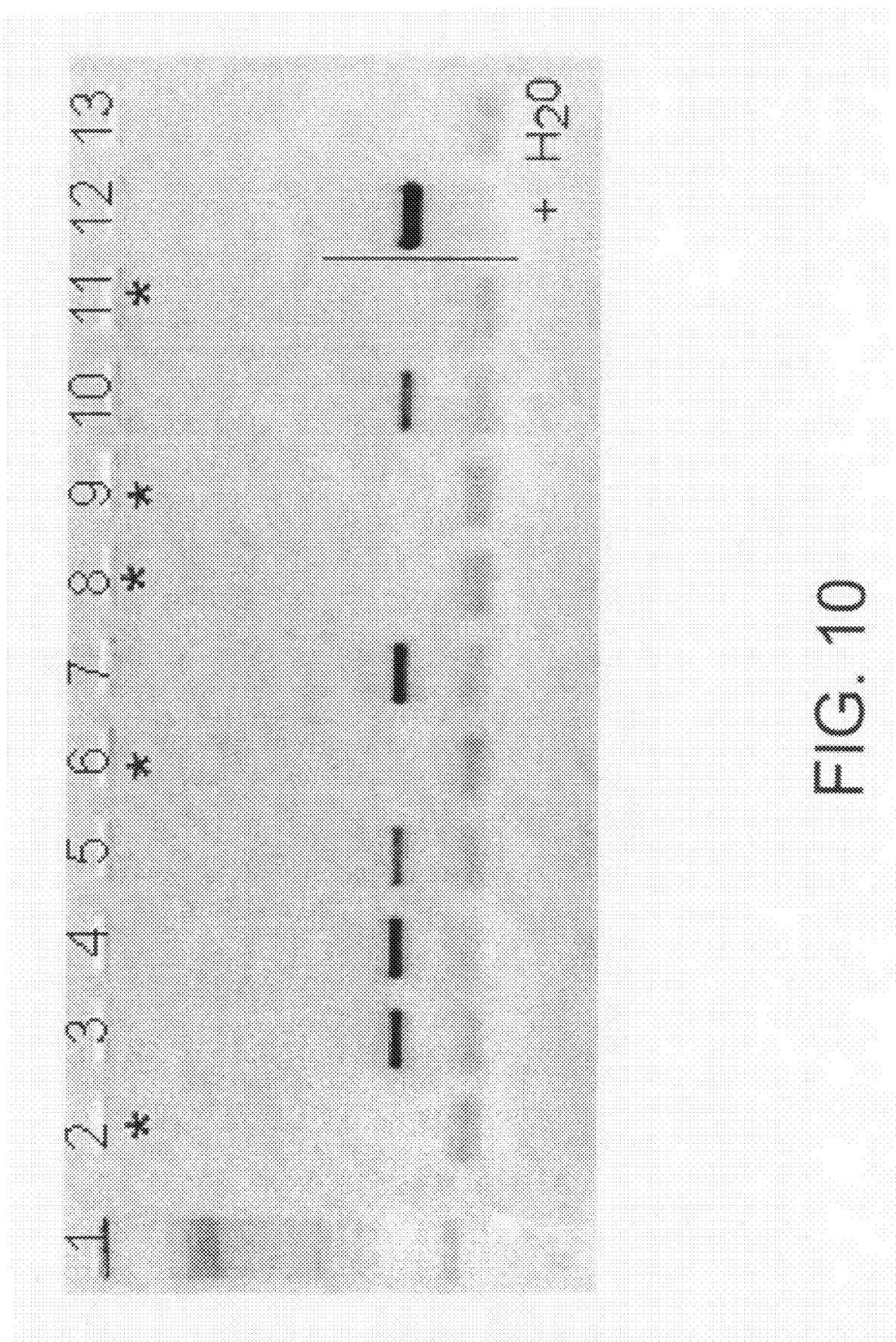
FIG. 10 shows ethidium bromide stained agarose gel showing the bands obtained by PCR analysis of the lateral suppressor gene of different DNA samples of tomato generated by the DNA extraction procedure according to this invention.
Lane 1: size marker,
Lanes 2 to 11: 10 individual tomato root border cell preparations, Lane 12: DNA from tomato leaf disc,
Lane 13: negative control, water.
Figure 11:
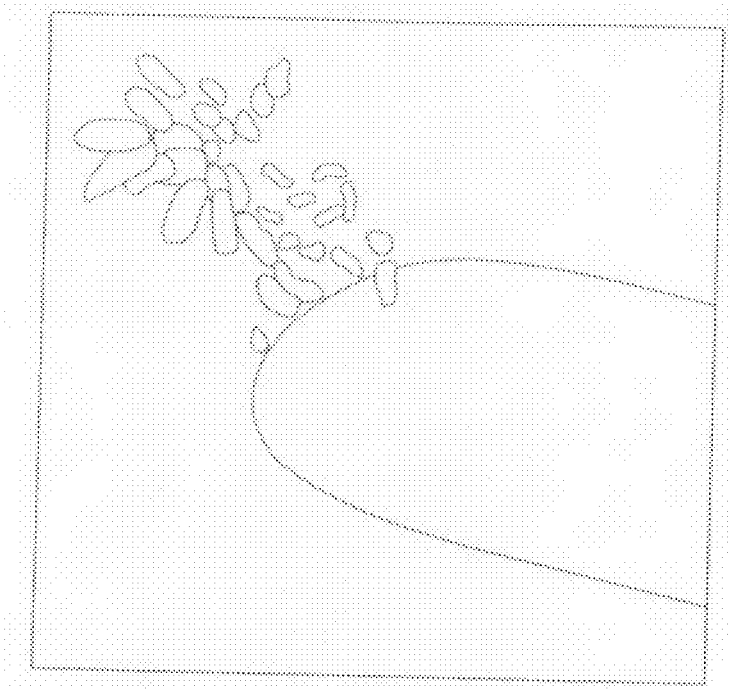
FIG. 11(a) shows root tip of $Brassica\ oleracea$ with attached root border cells.
FIG. 11(b) shows a schematic depicting the image of FIG. 11(a).
Figure 11:
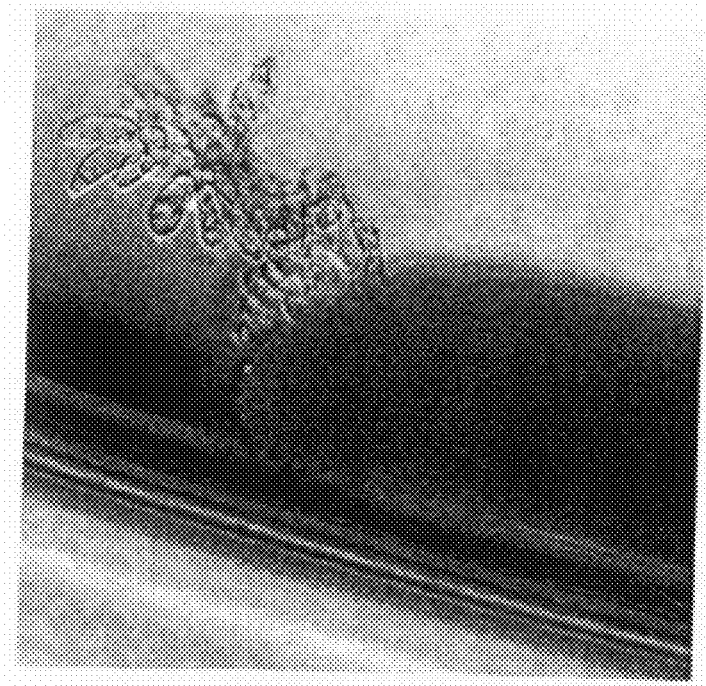
Figure 12:
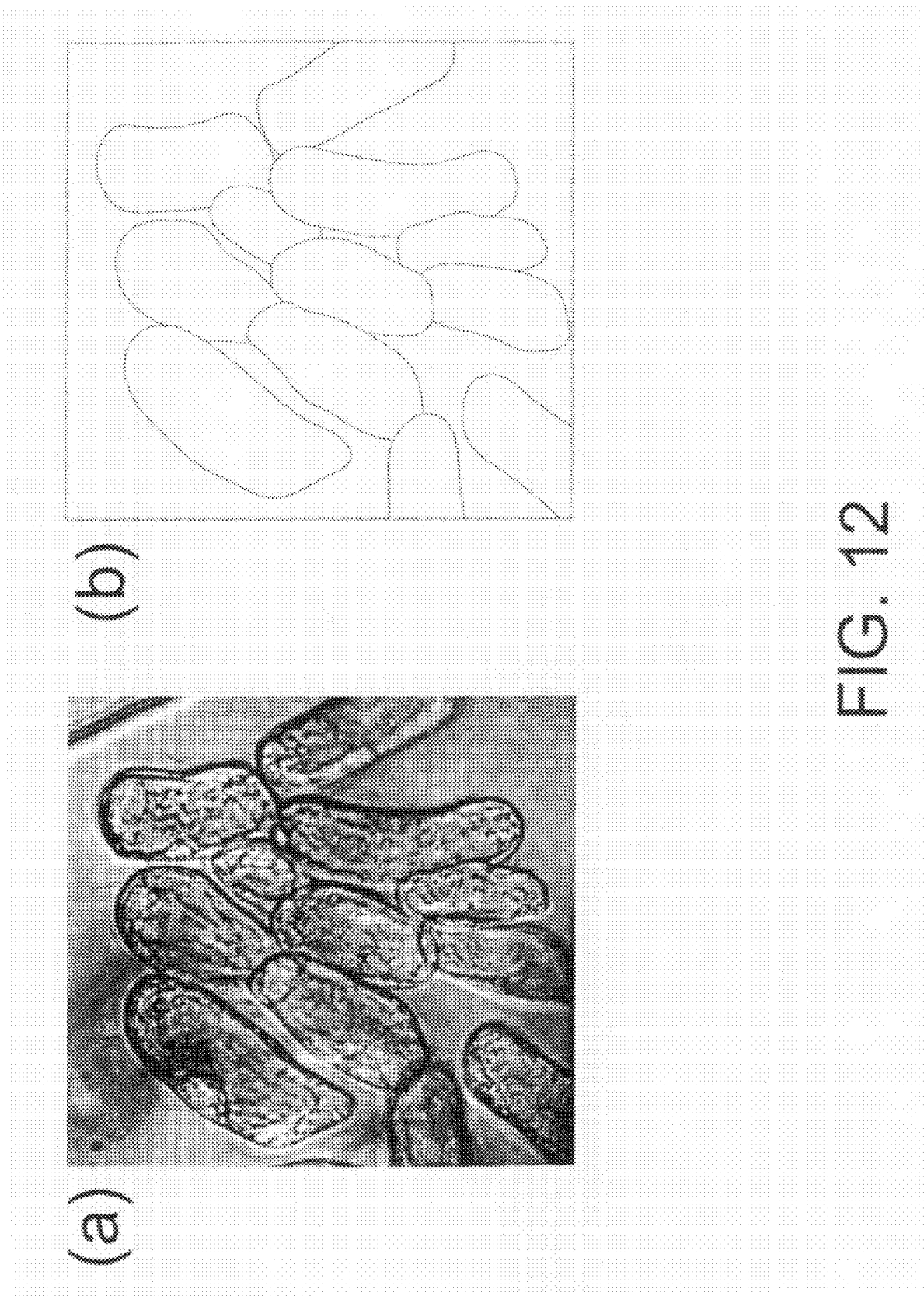
FIG. 12(a) shows a detailed view on root border cells of $Brassica\ oleracea$.
FIG. 12(b) shows a schematic depicting the image of FIG. 12(a).

PCR was carried using 5 Fl of total amount of DNA using a primer combination specific for a known gene of tomato called lateral suppressor which is anticipated to generate a band of 360 bp. The result of this experiment is shown in FIG. 10.

The results clearly demonstrate that the amount of DNA isolated by this procedure is sufficient to generate a PCR fragment of the expected size which can be detected on an agarose gel. It should be noted that in those cases in which no band was observed (lanes marked with asterisks in FIG. 10) the seed had not germinated. This shows that the detection of the PCR fragment using this procedure is dependent on the germination of the seeds.

Example 4

DNA Extraction and Analysis from Root Border Cells of *Brassica oleracea*

An experiment was conducted using germinated seeds from *Brassica oleracea*. The procedure taken is comparable to the one described in Example 1. The germination temperature was 21EC. FIGS. 11(a) and 11(b) and FIGS. 12(a) and 12(b) shows root border cells at the root tip of a *Brassica oleracea* seedling.

In order to demonstrate that the DNA extract obtained from root border cells can be used to detect nucleic acids residing in the nucleus, a primer combination was designed which can amplify a fragment of a gene involved in the biosynthesis of ethylene called $BoACO_2$.

The PCR reaction is anticipated to result in a fragment of 344 bp. The result of this analysis is shown in FIG. 13.

Figure 13:
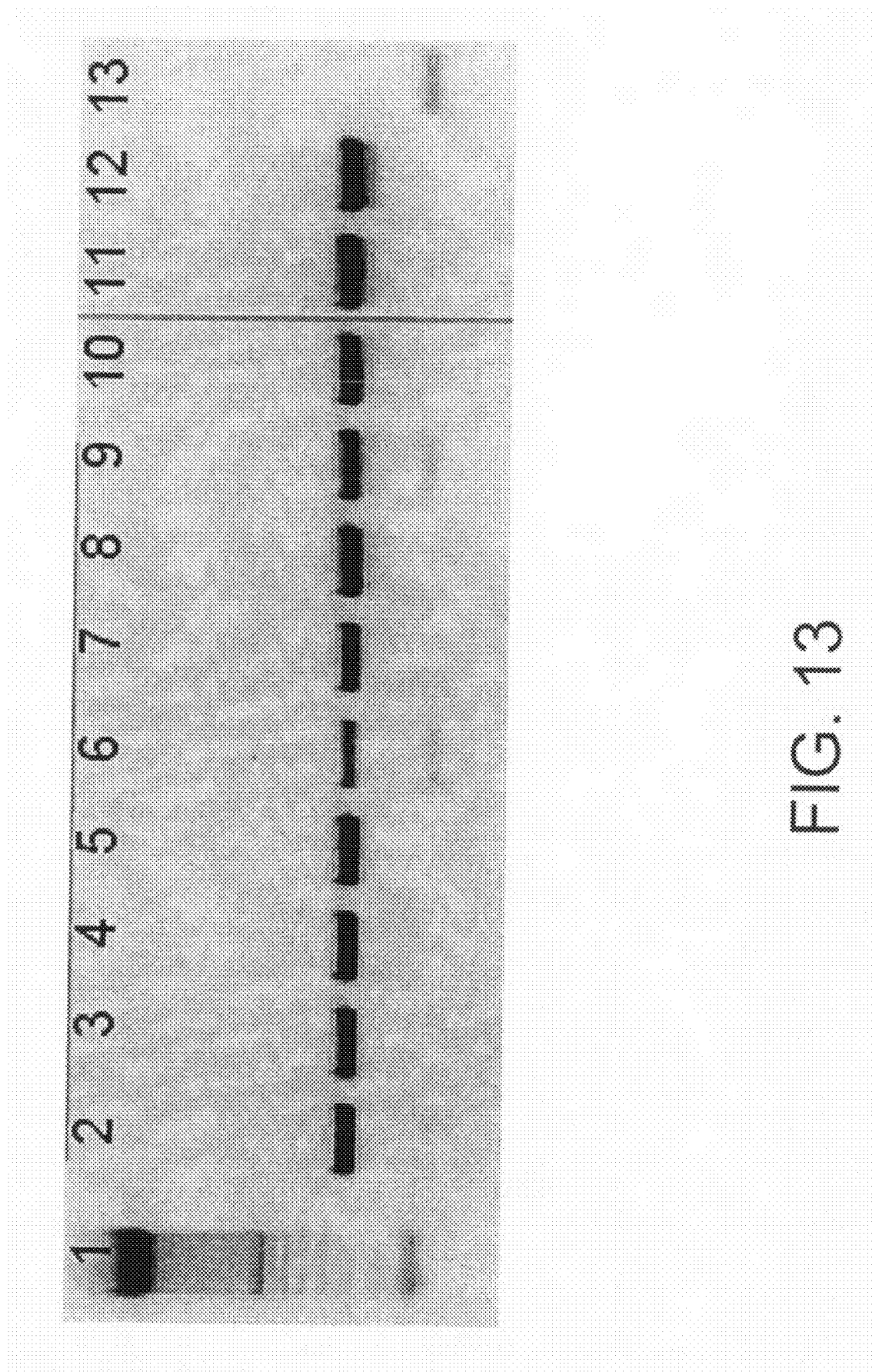
FIG. 13 shows ethidium bromide stained agarose gel showing the bands obtained by PCR analysis of the $BoACO_2$ gene fragment of different DNA samples of $Brassica\ oleracea$ generated by the DNA extraction procedure according to this invention.
Lane 1: size marker,
Lanes 2 to 12: 11 individual $Brassica\ oleracea$ root border cell preparations,
Lane 13: negative control, water.

The result shown in FIG. 13 demonstrates that sufficient DNA has been obtained in order to generate the expected nuclear DNA fragment by PCR.

Figure 14:
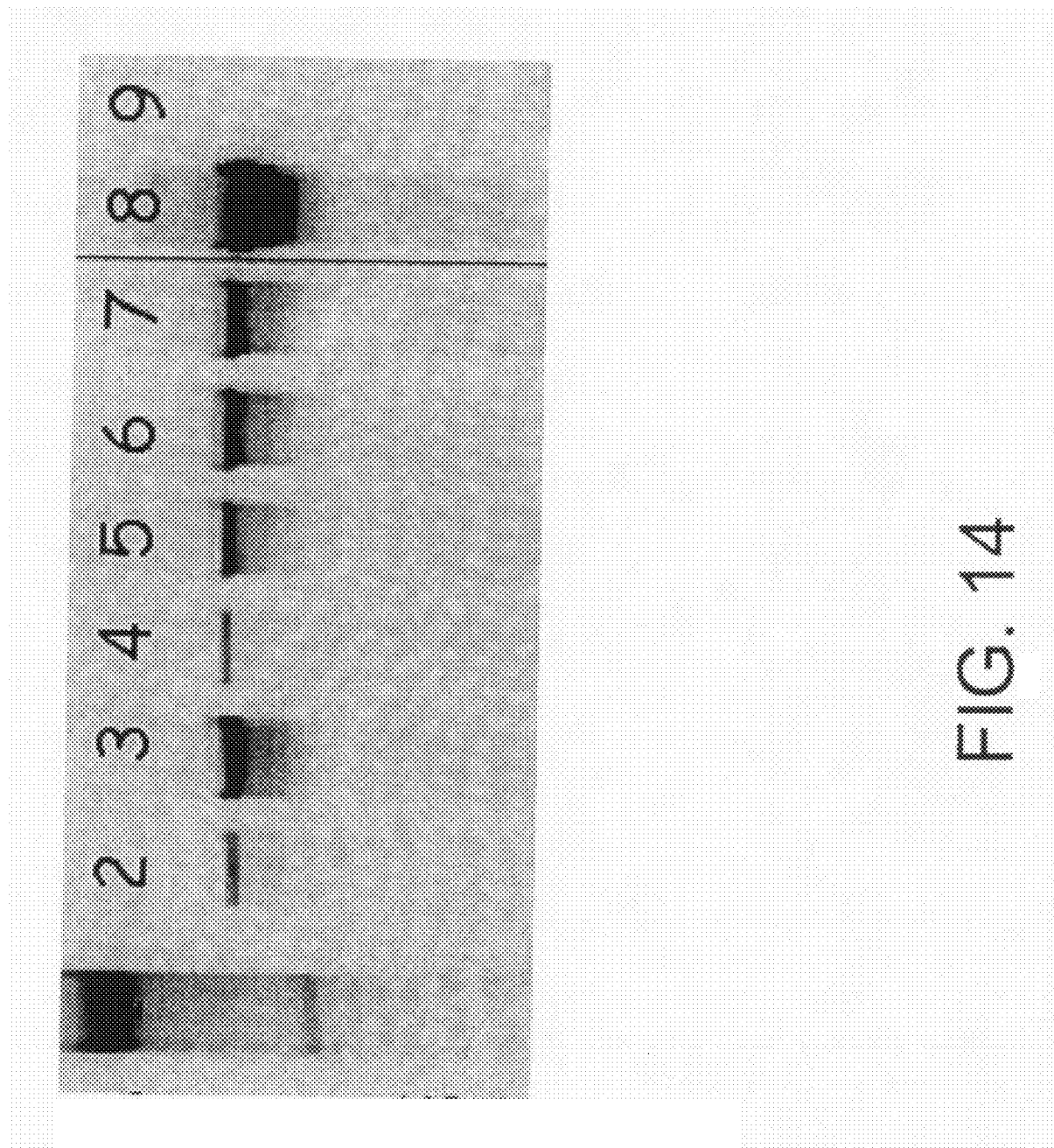
FIG. 14 shows ethidium bromide stained agarose gel showing the bands obtained by PCR analysis of the mitochondrial ORF B region of the mitochondrial genome of $Brassica\ oleracea$.
Lane 1: size marker,
Lanes 2 to 7: 6 individual $Brassica\ oleracea$ root border cell preparations,
Lane 8: DNA from a leaf of a $Brassica\ oleracea$ plant,
Lane 9: Negative control: water.

Another experiment was performed in order to demonstrate that in addition to nuclear sequences, sequences residing in the cytoplasmic genomes can be detected in the root border cell derived DNA. A PCR reaction was carried out which amplifies the ORF B gene region located in the mitochondrial genome. The fragment of the ORF B region has an expected size of 1180 bp. The result of this experiment is given in FIG. 14.

The result shows the generation of a band specific for the ORF B gene region and demonstrates cytoplasmic DNA sequences can be detected using the DNA isolation procedure described.

Example 5

DNA Extraction and Analysis from Root Border Cells of Lettuce

Figure 15:
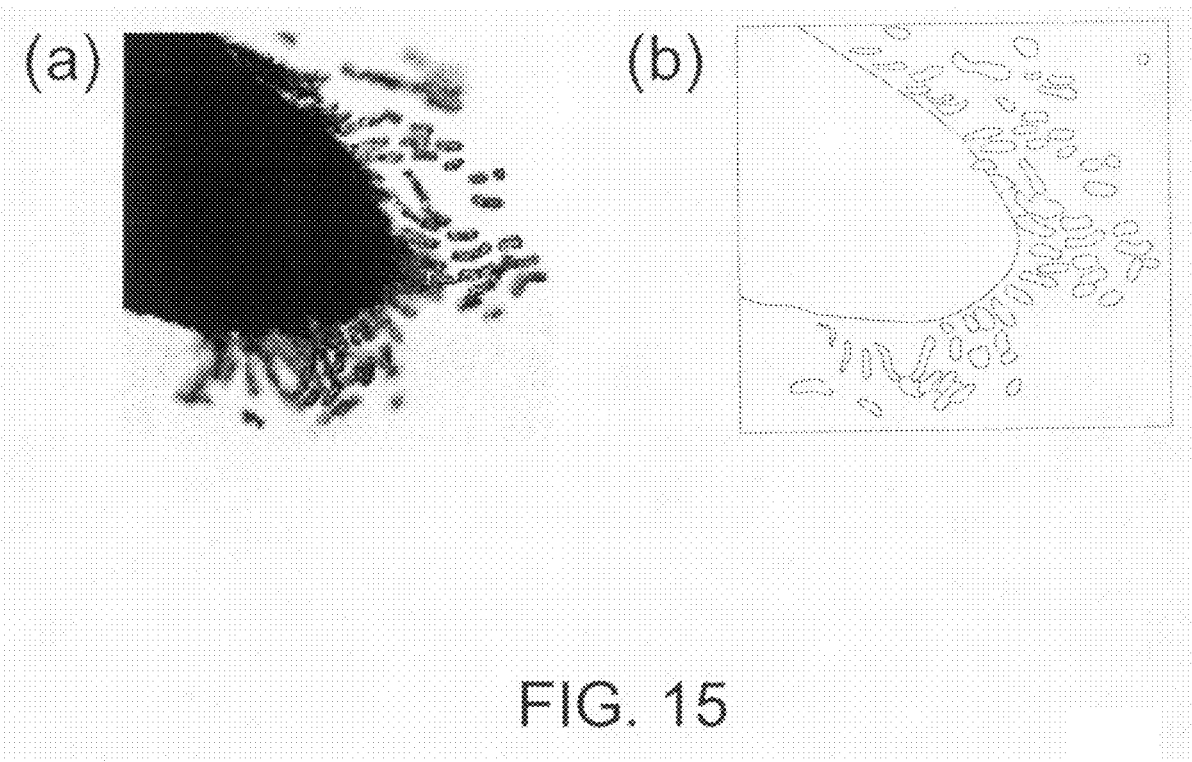
FIG. 15(a) shows light microscopy of root border cells shedded from a lettuce root after toluidine blue staining.
FIG. 15(b) shows a schematic depicting the image of FIG. 15(a).

Lettuce seeds were germinated at 21EC in 50 FL water (milliQ). Root emergence occurred within 2 days and root border cells were detached from the root by gentle shaking. The root border cells of lettuce visualised by microscopy are shown in FIGS. 15(a) and 15(b).

DNA extraction was carried out at a stage when the roots had an average length of approximately 1.5 cm. The DNA extraction procedure applied was similar to the one described for cucumber in Example 1. In order to assess whether sufficient DNA has been obtained, a PCR reaction was performed using a genomic marker, called NAS2, linked to the Nasonovia resistance gene. The result is given in FIG. 16.

The result shows the generation of a specific band of the expected size for the applied molecular marker when 5 Fl of the obtained DNA extract is used in the PCR reaction. It is concluded that the DNA isolation procedure according to this invention meets the requirements to carry out DNA analyses like PCR.

Figure 16:
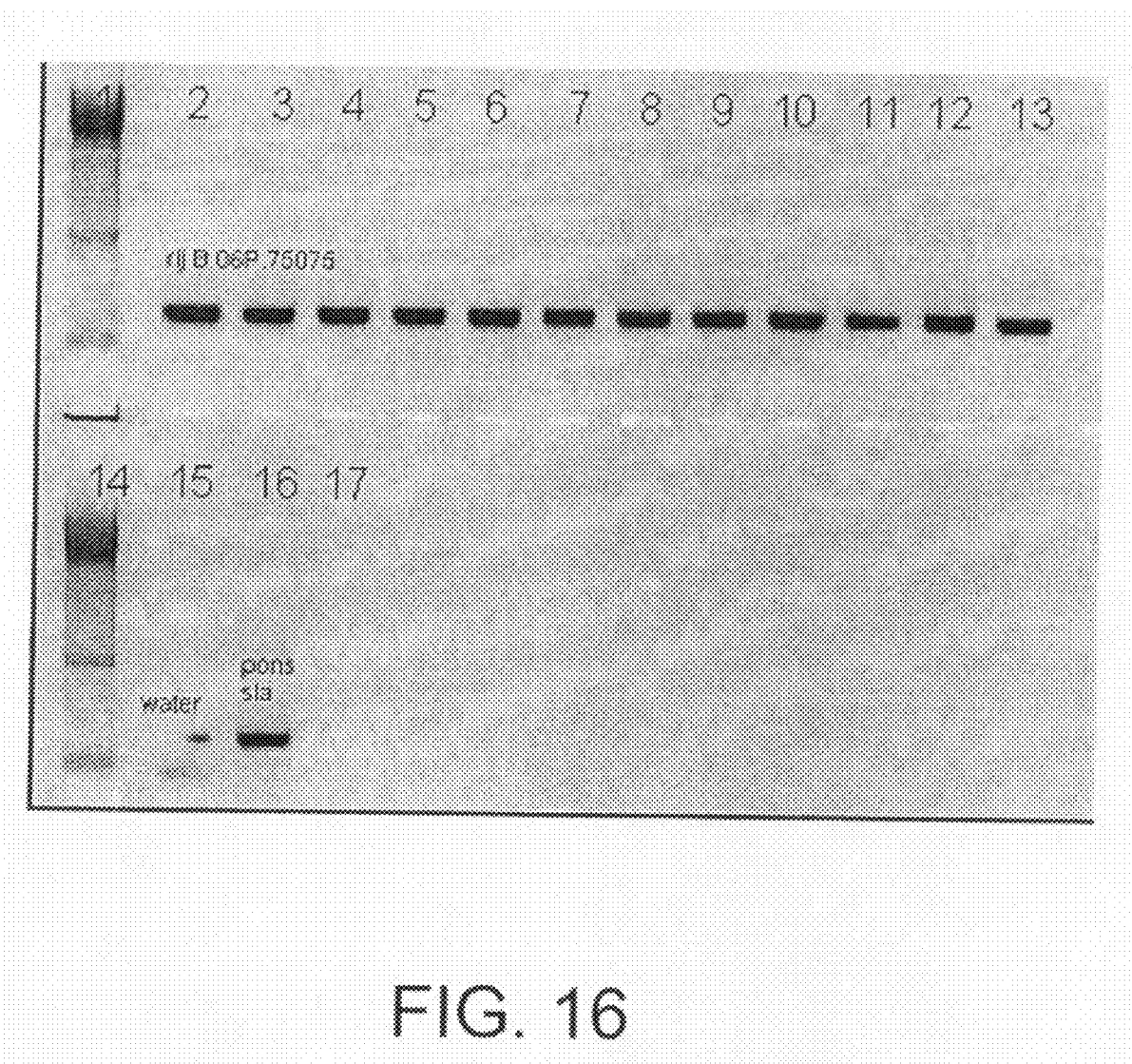
FIG. 16 shows ethidium bromide stained agarose gel showing the bands obtained by PCR analysis of the molecular marker linked to the Nasonovia resistance gene, called NAS2, of different DNA samples of lettuce generated by the DNA extraction procedure according to this invention.
Lane 1: size marker,
Lanes 2 to 13: 12 individual lettuce root border cell preparations,
Lane 14: size marker,
Lane 15: Negative control: water,
Lane 16: Positive control: DNA from a leaf disc of lettuce ("pons sla"),
Lane 17: negative control: DNA from cucumber.
Figure 17:
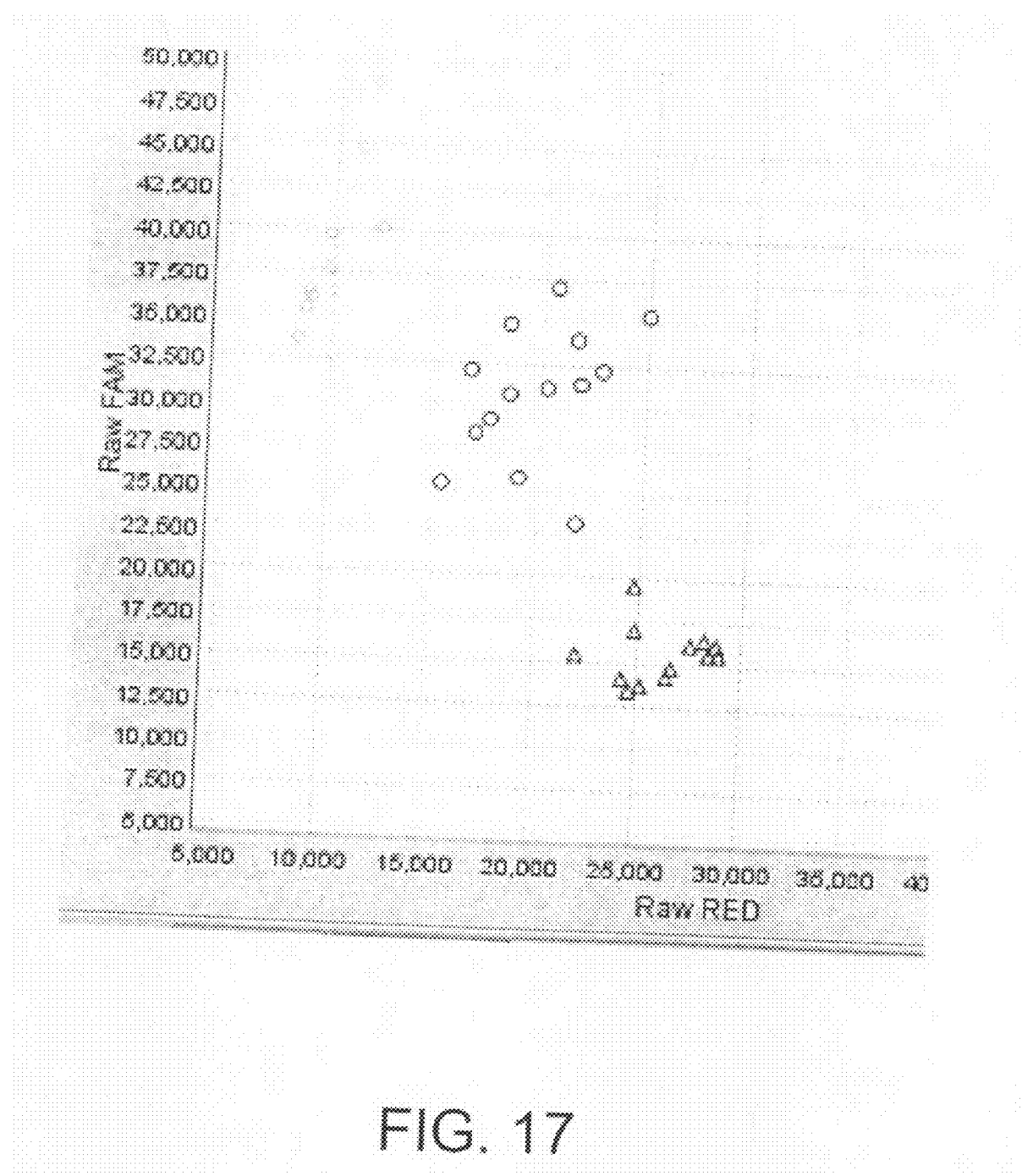
FIG. 17 shows FAM and RED scores expressed as raw values obtained after analysing lettuce root border cell DNA extracts using the NAS2-probe set. For each DNA sample the RED signal is plotted on the X-axis whereas the FAM signal is plotted on the Y-axis.

The result shown in FIG. 16 demonstrates that sufficient DNA has been obtained in order to generate the expected DNA fragment by PCR. To demonstrate that the fragment is indeed of embryonic origin, fluoresence-based NAS2 assay was carried out which detects both alleles of NAS2 present in the original hybrid and which are anticipated to segregate in the seeds used in this analysis. The results of this experiment are shown in FIG. 17.

The result clearly demonstrates segregation of the marker allele NAS2 into three classes: homozygous A (FAM signal), homozygous B (RED signal) and heterozygous which shows that the DNA is of embryonic origin.

Example 6

DNA from Root Exudates Resides in the DNase Resistant Fraction

In order to demonstrate that the DNA obtained from root exudate according to the procedure described by this invention originates from root border cells, DNase sensitivity experiments were conducted.

Root border cells were produced from cucumber seedlings as described in Example 1 and the isolated DNA was analysed by PCR using a primer combination specific for the marker locus kom24. The root exudate was treated with DNase before the DNA extraction was performed. In case the DNA is present in the root exudate as such it will be degraded by the DNase. In case the DNA is present inside the root border cells, the DNase treatment will not have an effect on the generation of a PCR signal after DNA extraction.

The result of this experiment is shown in FIGS. 18(a) and 18(b). The results show that exogenously added DNA from lettuce is sensitive to the DNase treatment when added to cucumber root exudates whereas the PCR signal of the cucumber DNA was not lost as a consequence of the DNase treatment. This demonstrates that the cucumber root exudate contains cucumber DNA which is protected from the added DNase and therefore is derived from root border cells present in the exudate.

Example 7

DNA Extraction Using Root Exudate from In Vitro Grown Plants

Figure 19:
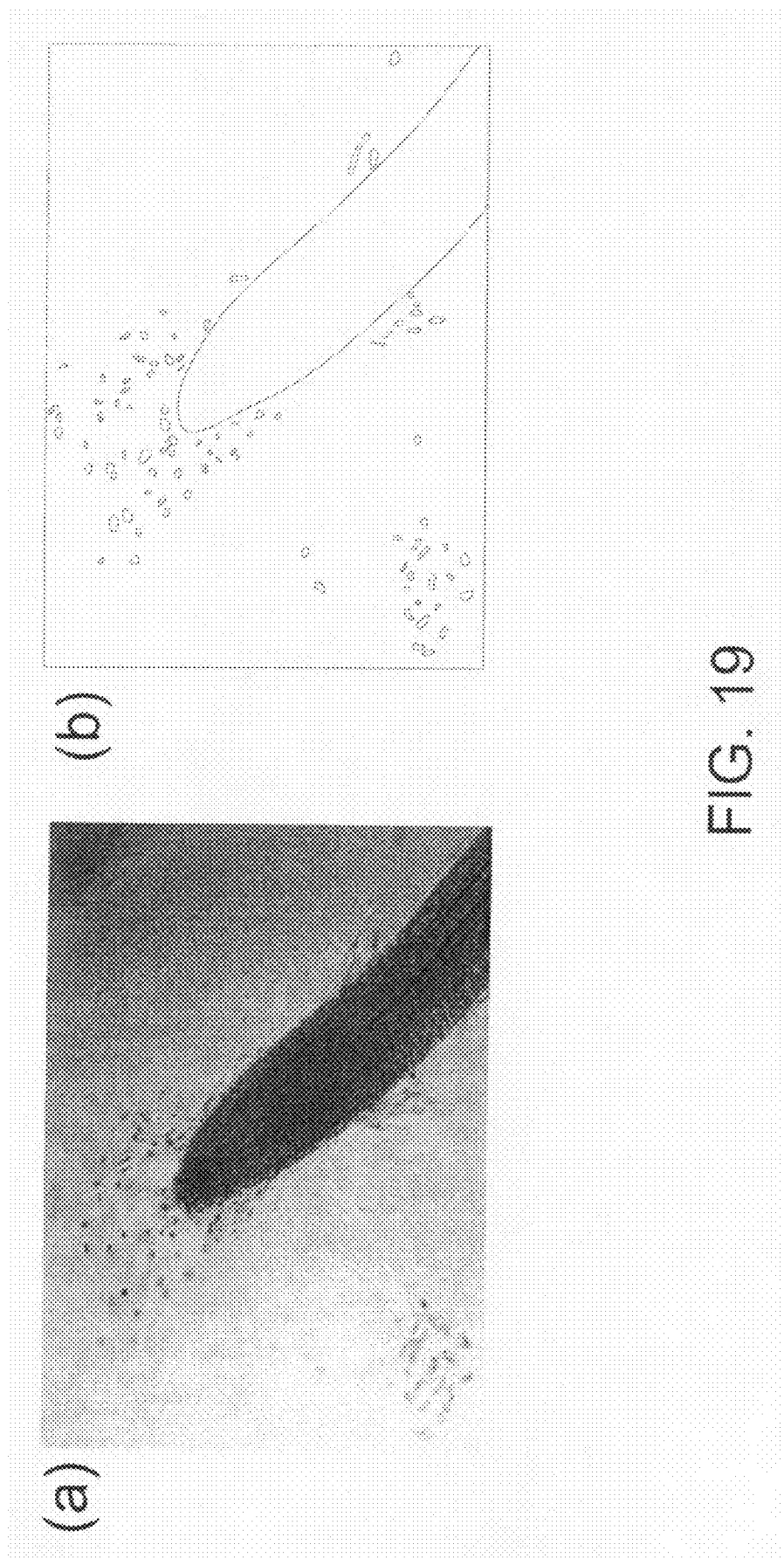
FIG. 19(a) shows a root tip of an adventitious root of an in vitro regenerated cucumber plant after incubation of 24 hours in water at 26EC. The shedding of root border cells is clearly visible at this stage.
FIG. 19(b) shows a schematic depicting the image of FIG. 19(a).

In vitro rooted shoots of cucumber were taken for analysis by transferring the plantlet from the in vitro culture medium into a water-containing macrowell plate allowing it to generate root border cells. After incubation for 24 hours at 26EC, the formation of root border cells was clearly visible by light microscopy as shown in FIGS. 19(a) and 19(b).

At this stage the root border cells were collected, DNA was extracted and analysed by PCR specific for the marker locus kom24. A clear band diagnostic for the presence of the cucumber genomic DNA was obtained using the DNA extract from the root border cells as shown in FIG. 20.

Figure 20:
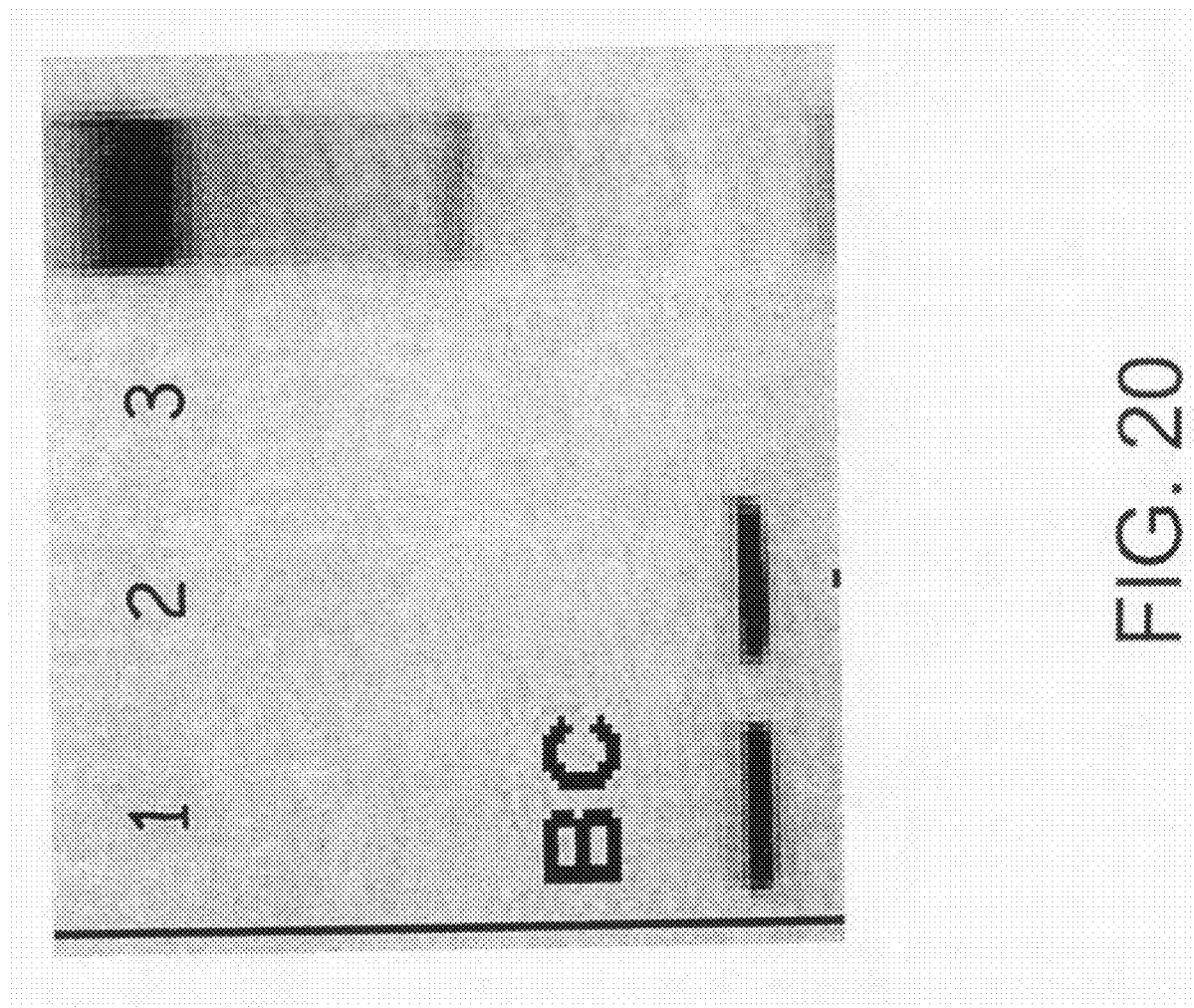
FIG. 20 shows ethidium bromide stained agarose gel showing the bands obtained by PCR analysis of the kom24 marker locus of different DNA samples of cucumber generated by the DNA extraction procedure according to this invention.

The result shown in FIG. 20 demonstrates that sufficient DNA has been obtained in order to generate the expected DNA fragment by PCR and therefore it can be concluded that the root border cell based DNA isolation technology is applicable to root exudate derived from adventitious roots from in vitro grown plantlets.

Example 8

DNA Extraction and Analysis from Root Border Cells of Pepper

Pepper seeds were germinated in 40 Fl water (milliQ) at 26EC and when the emerging roots had a length of on average 1.0 cm, DNA was extracted according to Example 1 of this application. Inspection by light microscopy clearly showed the presence of root border cells of pepper in the medium as shown in FIGS. 21(a) and 21(b).

The DNA preparations were analysed using a GMS-specific fluorescent probe set (Invader™) which generates a specific fluorescent signal (expressed as net Fold Over Zero or FOZ) for each of the GMS alleles (FAM or RED). In this example F1 hybrid seeds were analysed known to be uniformly heterozygous for the GMS marker allele. It is therefore expected that DNA preparations obtained according to the current invention from the individuals of the F1 hybrid population analysed using GMS-probes will generate fluorescent signals diagnostic for heterozygocity of the marker allele (plotted on the diagonal, RED+FAM signal). The result of the analysis is shown in FIG. 22.

The GMS genotypic scores obtained using the fluorescence based analysis of the population were found to be in accordance with the known phenotypic values for this marker locus for each plant analysed. Therefore, the results demonstrate that the amount of DNA isolated according to the procedure of this invention is adequate to carry out DNA marker analysis using fluorescence-based probe system as detection platform.

Example 9

Formation of Root Border Cells of Maize

Maize seeds were germinated in 500 Fl water (milliQ) at 21EC and when the emerging roots had a length of on average 2.0 cm, inspection by light microscopy clearly showed the presence of root border cells of maize in the medium as shown in FIGS. 23(a) and 23(b).

At this stage the root border cells were collected, DNA was extracted and analysed by PCR specific for the cell wall invertase (Incw1, accession number AF050129). A clear band of 620 bp diagnostic for the presence of the maize genomic DNA was obtained using the DNA extract from the root border cells as shown in FIG. 24.

Example 10

Formation of Root Border Cells of Endive

Endive seeds were germinated in 40 Fl water (milliQ) at 21EC and when the emerging roots had a length of on average 1.0 cm, inspection by light microscopy clearly showed the presence of root border cells of endive in the medium as shown in FIGS. 25(a) and 25(b).

Example 11

Formation of Root Border Cells of Carrot

Carrot seeds were germinated in 40 Fl water (milliQ) at 21EC and when the emerging roots had a length of on average 1.0 cm, inspection by light microscopy clearly showed the presence of root border cells of carrot in the medium as shown in FIGS. 26(a) and 26(b).

I claim:

1. A non-destructive method for obtaining DNA from a plant comprising:
   a) collecting root border cells from a growing root; and
   b) extracting DNA from the root border cells.
2. The method as claimed in claim 1, wherein the root border cells are contained in the root exudate of the growing root.
3. The method as claimed in claim 1, wherein the growing root is growing in a medium.
4. The method as claimed in claim 3, wherein the medium is water.
5. The method as claimed in claim 3, wherein the medium is tissue culture medium.
6. The method as claimed in claim 3, wherein the medium is soil.
7. The method as claimed in claim 1, wherein the growing root is part of a germinating seed.
8. The method as claimed in claim 1, wherein the growing root is the root of a seedling.
9. The method as claimed in claim 1, wherein the growing root is the adventitious root of a tissue culture plant or plant part.
10. The method as claimed in claim 7, wherein the seed is germinated until emergence of a radicle or root tip.
11. The method as claimed in claim 1, wherein the root border cells are collected from a root that has emerged about 1 to 2 cm.
12. The method as claimed in claim 1, wherein the root border cells are detached from the growing root.

* * * * *